US008097588B2

(12) United States Patent
Fukuda

(10) Patent No.: US 8,097,588 B2
(45) Date of Patent: Jan. 17, 2012

(54) TROPHININ-BINDING PEPTIDES AND USES THEREOF

(75) Inventor: Michiko Fukuda, LaJolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 722 days.

(21) Appl. No.: 12/026,810

(22) Filed: Feb. 6, 2008

(65) Prior Publication Data

US 2008/0200369 A1 Aug. 21, 2008

Related U.S. Application Data

(60) Provisional application No. 60/888,877, filed on Feb. 8, 2007.

(51) Int. Cl.
*A61K 38/00* (2006.01)
(52) U.S. Cl. ........................................................ 514/9.8
(58) Field of Classification Search .................. None
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,453,357 A | 9/1995 | Hogan | |
| 5,670,372 A | 9/1997 | Hogan | |
| 5,690,926 A | 11/1997 | Hogan | |
| 5,843,780 A | 12/1998 | Thomson | |
| 6,200,806 B1 | 3/2001 | Thomson | |
| 6,261,834 B1 | 7/2001 | Srivastava | |
| 6,709,659 B1 * | 3/2004 | Lok et al. ................... | 424/198.1 |
| 2004/0157292 A1 * | 8/2004 | Clapham et al. ............ | 435/69.1 |

FOREIGN PATENT DOCUMENTS

| | | |
|---|---|---|
| EP | 45665 | 2/1982 |
| WO | WO-8907136 A2 | 8/1989 |
| WO | WO-9002806 A1 | 3/1990 |
| WO | WO-9429348 | 12/1994 |
| WO | WO 0185753 | * 11/2001 |

OTHER PUBLICATIONS

U.S. Appl. No. 60/888,877.
Adachi et al. (2007) Crucial role of Bysl in mammalian preimplantation development as an integral factor for 40S ribosome biogenesis. Mol Cell Biol 27, 2202-14.
Almquist et al. (1980) Synthesis and biological activity of a ketomethylene analogue of a tripeptide inhibitor of angiotensin converting enzyme. J. Med. Chem. 23:1392-1398.
Aoki et al. (2006) The Bysl gene product, bystin, is essential for survival of mouse embryos. FEBS Lett 580, 6062-8.
Bagshawe et al. (1988) A cytotoxic agent can be generated selectively at cancer sites. Br. J. Cancer 58:700-703.
Bagshawe et al. (1989) The First Bagshawe lecture. Towards generating cytotoxic agents at cancer sites. Br. J. Cancer, 60:275-281.
Battelli et al. (1992) T lymphocyte killing by a xanthine-oxidase-containing immunotoxin. Cancer Immunol. Immunother., 35:421-425.
Benner et al. Expanding the genetic lexicon: incorporating non-standard amino acids into proteins by ribosome-based synthesis. (1994) TIB Tech, 12: 158-163.

Berkner et al.. (1987) Abundant expression of polyomavirus middle T antigen and dihydrofolate reductase in an adenovirus recombinant. J. Virology 61:1213-1220.
Blume-Jensen et al. (2001) Oncogenic kinase signalling. Nature 411, 355-65.
Bout et al. (1994) Lung gene therapy: in vivo adenovirus-mediated gene transfer to rhesus monkey airway epithelium. Human Gene Therapy 5:3-10.
Brenner et al. (1980) A study of 300 consecutive surgically treated cases. Jama 243, 673-6.
Brown et al. (1973) Penetration of host cell membranes by adenovirus 2. J. Virology 12:386-396.
Brown et al. (1991) Molecular and cellular mechanisms of receptor-mediated endocytosis. DNA and Cell Biology 10:6, 399-409.
Bucci et al. (2000) In vivo delivery of the caveolin-1 scaffolding domain inhibits nitric oxide synthesis and reduces inflammation. Nat. Med. 6, 1362-1367.
Cahill et al. Site-specific mutagenesis with unnatural amino acids. (1989) TIBS, 14(10):400-403.
Caillaud et al. (1993) Adenoviral vector as a gene delivery system into cultured rat neuronal and glial cells. Eur J. Neuroscience 5:1287-1291.
Carpenter et al. (2000) The EGF receptor: a nexus for trafficking and signaling, Bioessays 22, 697-707.
Carson et al. (2000) Embryo implantation. Dev. Biol. 223, 217-237.
Cavallaro et al. (2004) Multitasking in tumor progression: signaling functions of cell adhesion molecules. Ann. N.Y. Acad. Sci. 1014, 58-66.
Chardonnet et al. (1970) Early events in the interaction of adenoviruses with HeLa cells. I. Penetration of type 5 and intracellular release of the DNA genome. Virology 40:462-477.
Chen et al. (2003) Enp1, a yeast protein associated with U3 and U14 snoRNAs, is required for pre-rRNA processing and 40S subunit synthesis. Nucleic Acids Res 31, 690-9.
Chobotova et al. (2002) Heparin-binding epidermal growth factor and its receptor ErbB4 mediate implantation of the human blastocyst. Mech. Dev. 199, 137-44. Cotter et al. (1999) Molecular genetic analysis of herpesviruses and their potential use as vectors for gene therapy applications. Curr Opin Mol Ther 5: 633-644.
Creighton et al. (1983) Proteins: Structure and Molecular Properties, W.H. Freeman & Co., San Francisco pp. 79-86.
Das et al. (1994) Heparin-binding EGF-like growth factor gene is induced in the mouse uterus temporally by the blastocyst solely at the site of its apposition: a possible ligand for interaction with blastocyst EGF-receptor in implantation. Development 120, 1071-1083.
Davidson et al. (1987) Overproduction of polyomavirus middle T antigen in mammalian cells through the use of an adenovirus vector. J. Virology 61:1226-1239.
de Kretser et al. (2007) Male infertility. Lancet 349, 787-90.
Demott et al. (1992) Hyperactivated sperm progress in the mouse oviduct. Biol Reprod 46, 779-85.
Derossi et al. The third helix of the *Antennapedia homeodomain* translocates through biological membranes. (1994) Biol. Chem. 269, 10444-10450.
Elmquist et al. (2001) VE-cadherin-derived cell-penetrating peptide, pVEC, with carrier functions. Exp. Cell Res. 269, 237-244.
Enders et al. (1976) Cytology of human early implantation. Res Reprod 8, 1-2.

(Continued)

*Primary Examiner* — Cecilia J Tsang
*Assistant Examiner* — Thomas Heard
(74) *Attorney, Agent, or Firm* — Pabst Patent Group LLP

(57) ABSTRACT

Disclosed herein are compositions and methods useful for promoting sperm motility, promoting embryonic stem cell formation, promoting trophoblast formation, or promoting neuronal growth. The compositions and methods are based on peptide sequences that bind trophinin, inhibit bystin-mediated arrest of epidermal growth factor (EGF) receptor, and promotes EGF receptor autophosphorylation.

18 Claims, 18 Drawing Sheets

OTHER PUBLICATIONS

Enders et al. (1997) From blastocyst to placenta: the morphology of implanatation in the baboon,. Human Reprod. Update 12, 309-325.
Evans et al. (1981) Establishment in culture of pluripotential cells from mouse embryos. Nature 292:154-156.
Fischer et al. (2000) Structure-activity relationship of truncated and substituted analogues of the intracellular delivery vector Penetratin. J. Pept. Res. 55, 163-172.
Frankel et al. (1988) Cellular uptake of the tat protein from human immunodeficiency virus. Cell 55, 1189-1193.
Fukuda et al. (1995) Trophinin and tastin, a novel cell adhesion complex with potential involvement in embryo implantation. Genes & Develop. 9, 1199-1210.
Fukuda et al. (1999) Trophinin, tastin, and bystin: a complex mediating unique attachment between trophoblastic and endometrial epithelial cells at their respective apical cell membranes. Semin. Reprod. Endocrinol. 17,229-34.
Fukuda et al. (2000) A peptide mimic of E-selectin ligand inhibits sialyl Lewis X-dependent lung colonization of tumor cells. Cancer Res. 60, 450-6.
Fukuda et al. (2007) Signal transduction in human embryo implantation. Cell Cycle 6, 1153-6.
Gao et al. (2002) A cell-penetrating peptide from a novel pVII-pIX phage-displayed random peptide library. Bioorg. Med. Chem 10, 4057-4065.
Giancotti et al. (1999) Integrin signaling. Science 285, 1028-32.
Gomez-Foix et al. (1992) Adenovirus-mediated transfer of the muscle glycogen phosphorylase gene into hepatocytes confers altered regulation of glycogen metabolism. J. Biol. Chem. 267:25129-25134.
Green et al. (1988) Autonomous functional domains of chemically synthesized human immunodeficiency virus tat trans-activator protein. Cell 55, 1179-1188.
Guzman et al. (1993) Efficient gene transfer into myocardium by direct injection of adenovirus vectors. Circulation Research 73:1202-1207.
Haj-Ahmad et al. (1986) Development of a helper-independent human adenovirus vector and its use in the transfer of the herpes simplex virus thymidine kinase gene. J. Virology 57:267-274.
Hann et al. On the double bond isotere of the peptide bond: preparation of an enkephalin analogue. (1982) J. Chem. Soc Perkin Trans. I 307-314.
Hansen et al. (2002) the risk of major birth defects after intracytoplasmic sperm injection and in vitro fertilization. N Engl J Med 346, 725-30.
Hertig et al. (1956) A description of 34 human ova within the first 17 days of development. Am. J. Anat. 98, 435-93.
Hertig et al. (1973) Searching for early fertiliZed human ova. Gynecol. Invest. 4, 121-37.
Holladay et al. Synthesis of hydroxyethlyen and ketomethylene dipeptide isoteres. (1983) Tetrahedron. Lett 24:4401-4404.
Hong et al. (2000) Isolation of a peptide for targeted drug delivery into human head and neck solid tumors. Cancer Res. 60, 6551-6556.
Hruby et al. (1982) Conformational restrictions of biologically active peptides via amino acid side chain groups. Life Sci 31:189-199.
Hudson et al. Methionine enkephalin and isoteric analogues. (1979) Int J Pept Prot Res 14:177-185.
Hughes et al. (1989) Monoclonal antibody targeting of liposomes to mouse lung in vivo. Cancer Research 49:6214-6220.
Ibba et al. Towards engineering proteins by site-directed incorporation in vivo of non-natural amino acids. (1994) Biotechnology, 12:678-682.
Ibba et al. Strategies for in vitro and in vivo translation with non-natural amino acids. (1995) Biotechnology & Genetic Engineering Reviews 13:197-216.
Inoue et al. (2001 Developmental profile of neural cell adhesion molecule glycoforms with a varying degree of polymerization of polysialic acid chains. J Biol Chem 276, 31863-70.
Ishijima et al. (2002) Quantitative analysis of flagellar movement in hyperactivated and acrosome-reacted golden hamster spermatozoa. Mol Reprod Dev 61, 376-84.
Jennings et al. Synthesis of ketomethylene analogs of dipeptides. (1982) Tetrahedron Lett 23:2533.

Katz et al. (1980) Movement characteristics of hamster spermatozoa within the oviduct. Biol Reprod 22, 759-64.
Kirshenbaum et al. (1993) Highly efficient gene transfer into adult ventricular myocytes by recombinant adenovirus. J. Clin. Invest. 92:381-387.
Knoth et al. (1972) Ultrastructure of a human implantation site. Acta Obst. Gynecol. Scand. 51, 385-393.
Komuro et al. (2003) WW domain-containing protein YAP associates with ErbB-4 and acts as a co-transcriptional activator for the carboxyl-terminal fragment of ErbB-4 that translocates to the nucleus. J. Biol. Chem. 278, 33334-41.
Le Gal La Salle et al. (1993) An adenovirus vector for gene transfer into neurons and glia in the brain. Science 259:988-990.
Letsinger et al. (1989) Cholesteryl-conjugated oligonucleotides: synthesis, properties, and activity as inhibitors of replication of human immunodeficiency virus in cell culture. Proc. Natl. Acad. Sci. USA 86, 6553-6556.
Lin et al. (1995) Inhibition of nuclear translocation of transcription factor NF-kappa B by a synthetic peptide containing a cell membrane-permeable motif and nuclear localization sequence. J. Biol. Chem. 270, 14255-14258.
Lindenberg et al. (1986) Ultrastructure of the early human implantation in vitro. Human Reprod. 1, 533-538.
Litzinger et al. (1992) Biodistribution and immunotargetability of ganglioside-stabilized dioleoylphosphatidylethanolamine liposomes. Biochimica el Biophysica Acta, 1104:179-187.
Lundberg et al. (2002) Cell membrane translocation of the N-terminal (1-28) part of the prion protein. Biochem. Biophys. Res. Commun. 299, 85-90.
Martin et al. (1981) Isolation of a pluripotent cell line from early mouse embryos cultured in medium conditioned by teratocarcinoma stem cells. Proc. Natl. Acad. Sci. 78:7634-7638.
Massie et al.(1986) Construction of a helper-free recombinant adenovirus that expresses polyomavirus large T antigen. Mol. Cell. Biol. 6:2872-2883.
Millian et al. (1983) Antigenic determinants of human placental and testicular placental-like alkaline phosphatase as mapped by monoclonial antibodies. Enur. J. Biochem. 136, 1-7.
Misra et al. (2002) Gene targeting in the mouse: advances in introduction of transgenes into the genome by homologous recombination. Endocrine 19:229-238.
Miyoshi et al. (2007) Bystin in human cancer cells: intracellular localization and function in ribosome biogenesis. Biochem J 404, 373-81.
Morley et al. Modulation of the action of regulatory peptides by structural modification. (1980) Trends Pharm Sci pp. 463-468.
Morris et al. (2001) A peptide carrier for the delivery of biologically active proteins into mammalian cells. Nature Biotechnol. 19, 1173-1176.
Morsy et al. (1993) Efficient adenoviral-mediated ornithine transcarbamylase expression in deficient mouse and human hepatocytes. J. Clin. Invest. 92:1580-1586.
Moullier et al. (1993) Correction of lysosomal storage in the liver and spleen of MPS VII mice by implantation of genetically modified skin fibroblasts. Nature Genetics 4:154-158.
Mulligan The basic science of gene therapy. Science 260:926-932 (1993).
Nadano et al. (2002) Human tastin, a proline-rich cytoplasmic protein, associates with the microtubular cytoskeleton. Biochem. J. 364, 669-77.
Nakayama et al. (2003) Implantation-Dependent Expression of Trophinin by Maternal Fallopian Tube Epithelia during Tubal Pregnancies: Possible Role of Human Chorionic Gonadotrophin on Ectopi Pregnancy. Am. J. Pathol. 163, 2211-9.
Oehlke et al. (1998) Cellular uptake of an alpha-helical amphipathic model peptide with the potential to deliver polar compounds into the cell interior non-endocytically. Biochim. Biophys. Acta 1414, 127-139.
Okunade et al. (2004) Targeted ablation of plasma membrane Ca2+ATPase (PMCA) 1 and 4 indicates a major housekeeping function for PMCA1 and a critical role in hyperactivated sperm motility and male fertility for PMCA4. J Biol Chem 279, 33742-50.

Orsini et al. (1967) Loss of the zona pellucida in mice, and the effect of tubal ligation and ovariectomy. J. Reprod. Fertil. 13, 485-499.
Padykula et al. (1983) in Histology (ed Weiss, L.) 966-999 (Elsevier Biomedical, 1983).
Paria et al. (1999) Heparin-binding EGFlike growth factor interacts with mouse blastocysts independently of ErbB 1: a possible role for heparan sulfate proteoglycans and Erb/B4 n blastocyst implantation. Development 126, 1997-2005.
Paria et al. (2002) Deciphering the cross-talk of implantation: advances and challenges. Science 296, 2 185-8.
Park et al. (2000) Structure-activity analysis of buforin II, a histone H2A-derived antimicrobial peptide: the proline hinge is responsible for the cell-penetrating ability of buforin II. Proc. Natl Acad. Sci. USA 97, 8245-8250.
Pietersz et al. (1992) Antibody conjugates for the treatment of cancer. Immunolog. Reviews, 129:57-80.
Pooga et al. (1998) Cell penetration by transportan. FASEB J. 12, 67-77.
Ragot et al. (1993) Replication-defective recombinant adenovirus expressing the Epstein-Barr virus (EBV) envelope glycoprotein gp340/220 induces protective immunity against EBV-induced lymphomas in the cottontop tamarin. J. Gen. Virology 74:501-507.
Rich et al. (1993) Development and analysis of recombinant adenoviruses for gene therapy of cystic fibrosis. Human Gene Therapy 4:461-476.
Rizo et al. (1992) Constrained peptides: models of bioactive peptides and protein substructures. Ann. Rev. Biochem. 61:387.
Roessler et al. (1993) Adenoviral-mediated gene transfer to rabbit synovium in vivo. J. Clin. Invest. 92: 1085-1092.
Roffler et al. (1991) Anti-neoplastic glucuronide prodrug treatment of human tumor cells targeted with a monoclonal antibody-enzyme conjugate. Biochem. Pharmacol 42:2062-2065.
Rousselle et al. (2000) New advances in the transport of doxorubicin through the blood-brain barrier by a peptide vector-mediated strategy. Mol. Pharmacol. 57, 679-686.
Saburi et al. (2001) The trophinin gene encodes a novel group of MAGE proteins, magphinins, and regulates cell proliferation during gametogenesis in the mouse. J. Biol. Chem 276, 49378-49389.
Sawada et al. (2003) Cytoprotective membrane-permeable peptides designed from the Bax-binding domain of Ku70. Nature Cell Biol. 5, 352-357.
Senter et al. Generation of 5-fluorouracil from 5-fluorocytosine by monoclonal antibody-cytosine deaminase conjugates. (1991) Bioconjugate Chem. 2:447-451.
Senter et al. Generation of Cytotoxic Agents by Targeted Enzymes. (1993) Bioconjugate Chem. 4:3-9.
Seth et al. (1984) Role of a low-pH environment in adenovirus enhancement of the toxicity of a *Pseudomonas* exotoxin-epidermal growth factor conjugate. J. Virol. 51:650-655.
Seth et al. Evidence that the Penton base of adenovirus is involved in potentiation of toxicity of *Pseudomonas* extoxin conjugated to epidermal growth factor. (1984) Mol. Cell. Biol. 4:1528-1535.
Spatola et al. (1983) in /chemistry and Biochemistry of Amino Acids, Peptides and Proteins, B. Weinstein, eds., Marcel Dekker, New York, p. 267.
Spatola et al. (1986) Structure-activity relationships of enkephalins containing serially replaced thiomethylene amide bond surrogates. Life Sci 38:1243-1249.
Stewart et al. (2005) *Drosophilia* Bys is nuclear and shows dynamic tissue-specific expression during development. Dev Genes Evol 215, 97-102.
Suarez et al. (2003) Hyperactivated motility in sperm. Reprod Domest Anim 38, 119-24.
Sugihara et al. (2007) Trophoblast cell activation by trophinin ligation is implicated in human embryo implantation. Proc Ntl Acad Sci U S A 104, 3799-808.
Summers et al. (1971) Adenosine triphosphate-induced sliding of tubules in trypsin-treated *flagella* of sea-urchin sperm. Proc Natl Acad Sci U S A 68, 3092-6.
Sun et al. (1994) Human artificial episomal chromosomes for cloning large DNA fragments in human cells. Nature genetics 8: 33-41.
Suzuki et al. (1998) A novel cytoplasmic protein, bystin, interacts with trophinin, tastin and cytokeratin, and ma be involved in trophinin mediated cell adhesion between trophoblast and endometrial epithelial cells. Proc. Natl. Acad. Sci. USA 95, 5027-5032.
Suzuki et al. (1999) Expression of trophinin, tastin, and bystin by trophoblast and endometrial cells in human placenta. Biol. Repriod. 60, 621-627.
Suzuki et al. (2000) Trophinin expression in the mouse uterus coincides with implantation and is hormonally regulated but not induced by implanting blastocysts. Endocrinology 141, 4247-54.
Svensson et al. (1985) Role of vesicles during adenovirus 2 internalization into HeLa cells. J. Virology 55:442-449.
Swaffield et al. (1996) In Current Protocol in Molecular Biology 20.2.1-20.2.10 (John Wiley & Sons, Inc. 1996).
Tada et al. (1999) A common signaling pathway via Syk and Lyn tyrosine kinases generated from capping of the sialomucins CD34 and CD43 in immature hematopoietic cells. Blood 93, 3723-35.
Thorson et al. A biosynthetic approach for the incorporation of unnatural amino acids into proteins. (1991) Methods in Molec. Biol. 77:43-73.
Threadgill et al. (1995) Targeted disruption of mouse /EGF receptor: effect of genetic background on mutant phenotype. Science 269, 230-4.
Turner et al. (2003) Tales from the tail: what do we really know about sperm motility? J Androl 24, 790-803.
Van Steirteghem et al. (1993) High fertilization and implantation rates after intracytoplasmic sperm injection. Hum Reprod 8, 1061-6.
Varga et al. (1991) Infectious entry pathway of adenovirus ype 2. J. Virology 65:6061-6070.
Verma, I.M., Retroviral vectors for gene transfer. In Microbiology—1985, American Society Microbiology, pp. 229-232, Washington (1985).
Vigneron et al. (1998) Guanidinium-cholesterol cationic lipids: efficient vectors for the transfection of eukaryotic cells. Proc. Natl. Acad. Sci. USA 93, 9682-9686.
Wickham et al. (1993) Integrins alpha v beta 3 and alpha v beta 5 promote adenovirus internalization but not virus attachment. Cell 73:309-319.
Wolf et al. (2004) Use of assisted reproductive technologies in the propagation of rhesus macaque offspring Biol. Reprod. 71, 486-93.
Wolff et al. (1990) Direct gene transfer into mouse muscle in vivo. science, 247, 1465-1468.
Wolff et al. (1991) Human dystrophin expression in mdx mice after intramuscular injection of DNA constructs. Nature 352, 815-818.
Yanagimachi et al. (1970) The movement of golden hamster spermatozoa before and after capacitation. J Reprod Fertil 23, 193-6.
Zabner et al. (1993) Adenovirus-mediated gene transfer transiently corrects the chloride transport defect in nasal epithelia of patients with cystic fibrosis. Cell 75:207-216.
Zabner et al. (1994) Safety and efficacy of repetitive adenovirus-mediated transfer of CFTR cDNA to airway epithelia of primates and cotton rats. Nature Genetics 6:75-83.
Zelinski et al. (1995) Follicle stimulating hormone alone supports follicle growth and oocyte development in gonadotrophin-releasing hormone antagonist-treated monkeys. Hum. Reprod. 10, 1658-66.
Zhang et al. (1993) "Generation and identification of recombinant adenovirus by liposome-mediated transfection and PCR analysis" BioTechniques 15:868-872.
Zoller et al. (1992) New recombinant DNA methodology for protein engineering. Current Opinion in Biotechnology, 3:348-354.
Fukuda et al. (2007) The role of bystin in embryo implantation and in ribosomal biogenesis. Cell Mol Life Sci, Oct. 6; p. 1-8.
Nadano et al. (2002) Significant differences between mouse and human trophinins are revealed by their expression patterns and targeted disruption of mouse trophinin. Biol Reprod 66:313-21.
Bavister et al. The effects of sperm extracts and energy sources on the motility and acrosome reaction of hamster spermatozoa in vitro. Biol Reprod. 16, 228-37 (1977).
Koivunen et al. Isolation of highly specific ligand for the alpha 5 beta 1 integrin from a phage display library. J Cell Biol 124:373-80 (1994).
McKiernan et al. Culuture of on-cell hamster embroys with water soluble vitamins: pantothenate stimulates blastocyst production. Hum Reprod 15:157-64 (2000).

Narisawa et al. Testis-specific cytochrome c-null mice produce funtional sperm but undergo early testicular atrophy. Mol Cell Biol 22, 5554-62 (2002).

Qi et al. All four CatSper ion channel proteins are requried for male fertility and sperm cell hyperactivated motility. PNAS 104:1219-23, 2007.

Schuh et al. Plasma membrane Ca2+ ATPase 4 is required for sperm motility and male fertility. J Biol Chem 279:28220-6 (2004).

Yamaguchi et al. Golgi retention mechanism of beta-1,4-galactosyltransferase. Membrane spanning domain dependent homodimerization and association with alpha- and beta-tubulins. J Biol Chem 270:12170-12176, 1995.

International Search Report for PCT/US08/53158 dated Jan. 14, 2009.

International Preliminary Report on Patentability and Written Opinion for PCT/US08/53158 dated Aug. 11, 2009.

* cited by examiner

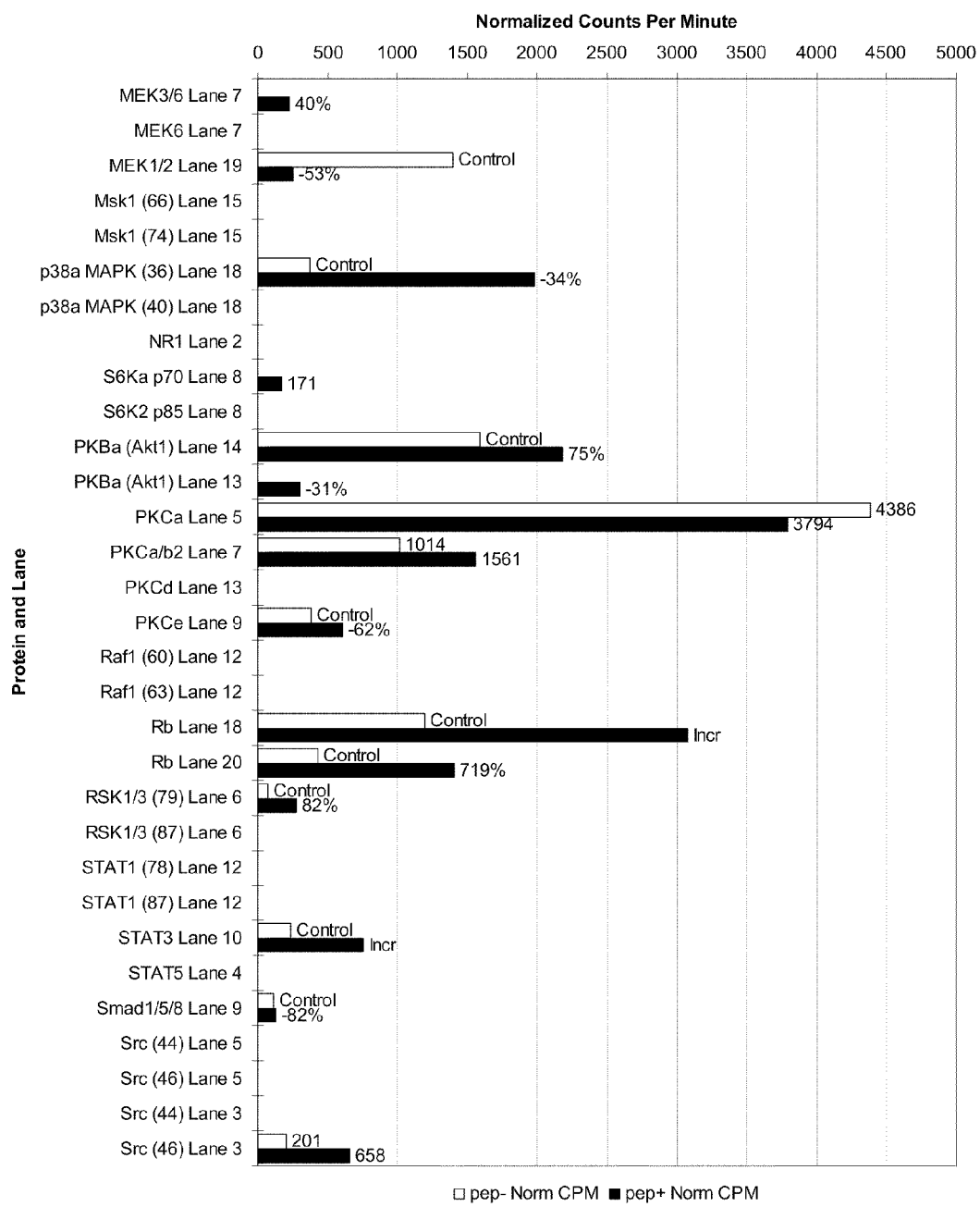
Fig. 4(cont...)

SEQUENCE LISTING

```
<160> NUMBER OF SEQ ID NOS: 41

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1
<223> OTHER INFORMATION: Xaa = G, A, L, I, T, or S
<220> FEATURE:
<221> NAME/KEY: VARIANT
<222> LOCATION: 2
<223> OTHER INFORMATION: Xaa = W or Y
<220> FEATURE:
<221> NAME/KEY: VARIANT
<222> LOCATION: 3
<223> OTHER INFORMATION: Xaa = R, K, or H
<220> FEATURE:
<221> NAME/KEY: VARIANT
<222> LOCATION: 4
<223> OTHER INFORMATION: Xaa = Q or N

<400> SEQUENCE: 1

Xaa Xaa Xaa Xaa
 1

<210> SEQ ID NO 2
<211> LENGTH: 4
<212> TYPE: PRT
<213> ORGANISM: Artificial Sequence
```

```
<220> FEATURE:
<223> OTHER INFORMATION: Description of Artificial Sequence; note =
      synthetic construct

<400> SEQUENCE: 2

Gly Trp Arg Gln
 1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1
<223> OTHER INFORMATION: Xaa = G, A, L, I, T, or S
<220> FEATURE:
<221> NAME/KEY: VARIANT
<222> LOCATION: 2
<223> OTHER INFORMATION: Xaa = W or Y
<220> FEATURE:
<221> NAME/KEY: VARIANT
<222> LOCATION: 3
<223> OTHER INFORMATION: Xaa = R, K, or H
<220> FEATURE:
<221> NAME/KEY: VARIANT
<222> LOCATION: 4
<223> OTHER INFORMATION: Xaa = Q or N
<220> FEATURE:
<221> NAME/KEY: VARIANT
<222> LOCATION: 5
<223> OTHER INFORMATION: Xaa = S, A, V, or L

<400> SEQUENCE: 3

Xaa Xaa Xaa Xaa Xaa
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Gly Trp Arg Gln Leu Thr Ala Arg Val Pro
 1               5                  10

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
acaggtgcga atgacagtag cat                                           23

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
```

```
accatttctt ccttgataaa ttggatg                                          27
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 7

```
caaattagga accttgcaac ggt                                              23
```

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 8

```
tcccctgggt ctttatttcg tc                                               22
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 9

```
ttgataaccc tgattactgg catagc                                           26
```

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10

```
tgagaggaag ggatatggag agtaatc                                          27
```

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11

```
gaataggaac cagtttgtat accgag                                           26
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12

```
cttgtttggg tttgtctcgc at                                               22
```

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence; note = synthetic construct

<400> SEQUENCE: 13
acccgggaaa gagcatcaaa aagaaaag                                    28

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence; note = synthetic construct

<400> SEQUENCE: 14
ggcagccatg gggcataa                                               18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence; note = synthetic construct

<400> SEQUENCE: 15
caacttatgc cccatggct                                              19

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence; note = synthetic construct

<400> SEQUENCE: 16
atcatatctt ccaaatcctc ttcatc                                      26

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence; note = synthetic construct

<400> SEQUENCE: 17
atcgtatgaa gcttcccagt cc                                          22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence; note = synthetic construct

<400> SEQUENCE: 18
aactgagctt acaccacagt attcc                                       25

```
<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Ser Ser Leu Met Leu Gly Gly Trp Arg Gln
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20

Ser Leu Ser Val Gly Trp Arg Gln Ser Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

Leu Ser Leu Arg Gly Tyr Arg Gln Ala Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 22

Val Leu Trp Arg Gly Val Ala Gly Arg Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 23

Gly Trp Arg Gln Leu Thr Ala Arg Val Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 24
```

```
Thr Trp Arg Tyr Leu Arg Ser Pro Gln Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 25

Ser Lys Gly Trp Lys His Trp Thr Pro Arg
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 26

Arg Gln Pro Lys Ile Trp Phe Pro Asn Arg Arg Lys Pro Trp Lys Lys
1               5                   10                  15

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 27

Gly Arg Lys Lys Arg Arg Gln Arg Pro Pro Gln
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 28

Arg Gln Ile Lys Ile Trp Phe Gln Asn Arg Arg Met Lys Trp Lys Lys
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 29

Arg Gln Ile Ala Ile Trp Phe Gln Asn Arg Arg Met Lys Trp Ala Ala
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence; note =
``` synthetic construct

<400> SEQUENCE: 30

Arg Lys Lys Arg Arg Gln Arg Arg Arg
1               5

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 31

Thr Arg Ser Ser Arg Ala Gly Leu Gln Phe Pro Val Gly Arg Val His
1               5                   10                  15

Arg Leu Leu Arg Lys
            20

<210> SEQ ID NO 32
<211> LENGTH: 26
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 32

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 33

Lys Leu Ala Leu Lys Leu Ala Leu Lys Ala Leu Lys Ala Ala Leu Lys
1               5                   10                  15

Leu Ala

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 34

Ala Ala Val Ala Leu Leu Pro Ala Val Leu Leu Ala Leu Leu Ala Pro
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

```
<400> SEQUENCE: 35

Val Pro Met Leu Lys Pro Met Leu Lys Glu
1               5                   10

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 36

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 37

Leu Leu Ile Ile Leu Arg Arg Arg Ile Arg Lys Gln Ala His Ala His
1               5                   10                  15

Ser Lys

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 38

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 39

Arg Gly Gly Arg Leu Ser Tyr Ser Arg Arg Phe Ser Thr Ser Thr
1               5                   10                  15

Gly Arg

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct
```

```
<400> SEQUENCE: 40

Ser Asp Leu Trp Glu Met Met Met Val Ser Leu Ala Cys Gln Tyr
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 41

Thr Ser Pro Leu Asn Ile His Asn Gly Gln Lys Leu
1               5                   10
```

TROPHININ-BINDING PEPTIDES AND USES THEREOF

CROSS-REFERENCE TO RELATED APPLICATIONS

This application claims benefit of U.S. Provisional Application No. 60/888,877, filed Feb. 8, 2007, which is hereby incorporated herein by reference in its entirety.

STATEMENT REGARDING FEDERALLY SPONSORED RESEARCH

This invention was made with government support under grant HD34 108 awarded by the National Institutes of Health and grant W81XWH-04-1-0917 awarded by the Department of Defense. The government has certain rights in the invention.

BACKGROUND

A fertilized mammalian egg autonomously develops into a blastocyst, which must be successfully implanted in the uterus. In higher primates including humans, trophectoderm cells at the embryonic pole adhere to the maternal epithelium (Hertig, A T, et al. 1956; Hertig, A T, et al. 1973; Padykula, H A. 1983; Enders, A C, et al. 1997). Apically-adhered trophectoderm cells rapidly grow and invade maternal tissue (Hertig, A T, et al. 1973; Knoth, M, et al. 1972; Enders, A C. 1976; Lindenberg, S, et al. 1986), suggesting that a mechanism triggered by adhesion stimulates silent trophectoderm to form an active trophoblast. Embryo implantation is unique to mammals; however, the process of implantation differs significantly among species (Carson, D D, et al. 2000). Some mechanisms underlying human embryo implantation are likely unique; for example, ectopic implantation is not rare in humans (Brenner, P F, et al. 1980), while it does not occur in other animals (Orsini, M W. et al. 1967).

Male infertility can result from a deficiency in sperm motility. In a normal human semen sample there are approximately $4\text{-}40 \times 10^7$ sperm, which upon ejaculation swim actively forward, cross through the uterine cervix to the opening of the fallopian tube, wherein about 250 sperm reach the fertilization site by chemotaxis. In the uterus, sperm become capacitated (i.e., capable to fertilize), acquire the ability to undergo the acrosome reaction (AR) and become hyperactivated. This hyperactivation is required for the sperm to penetrate the egg's extracellular matrix (zona pellucida). When sperm reach the isthmus in the oviduct female reproductive tract they slow down and resume their hyperactivated motility only after ovulation, probably due to the rise in progesterone and other yet undefined chemical attractants. The various cycles and forms of sperm motility occurring inside the female reproductive tract suggest that biochemical processes regulate each phase of the spermatozoa life cycle and that male fertility is partially dependent on factors present in the female genital tract. Thus, there is a widely recognized need for methods and compositions suitable for enhancing male fertility and promoting trophoblast formation.

BRIEF SUMMARY

In accordance with the purpose of this invention, as embodied and broadly described herein, this invention relates to compositions and methods for binding trophinin.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 shows identification of short peptides with trophinin binding activity on HT-H cell surfaces.

FIG. 2 show interaction between trophinin and EGF receptor.

FIG. 3 show expression of EGFRs in HT-H cells and tyrosine phosphorylation of ErbB4 by GWRQ.

FIG. 10 shows effect of MAPS (Multiple Antigen Peptide System) peptides on human sperm motility.

FIG. 11 shows effect of GWRQ peptide on ATP and intracellular calcium of human sperm.

DETAILED DESCRIPTION

Figure 1A:
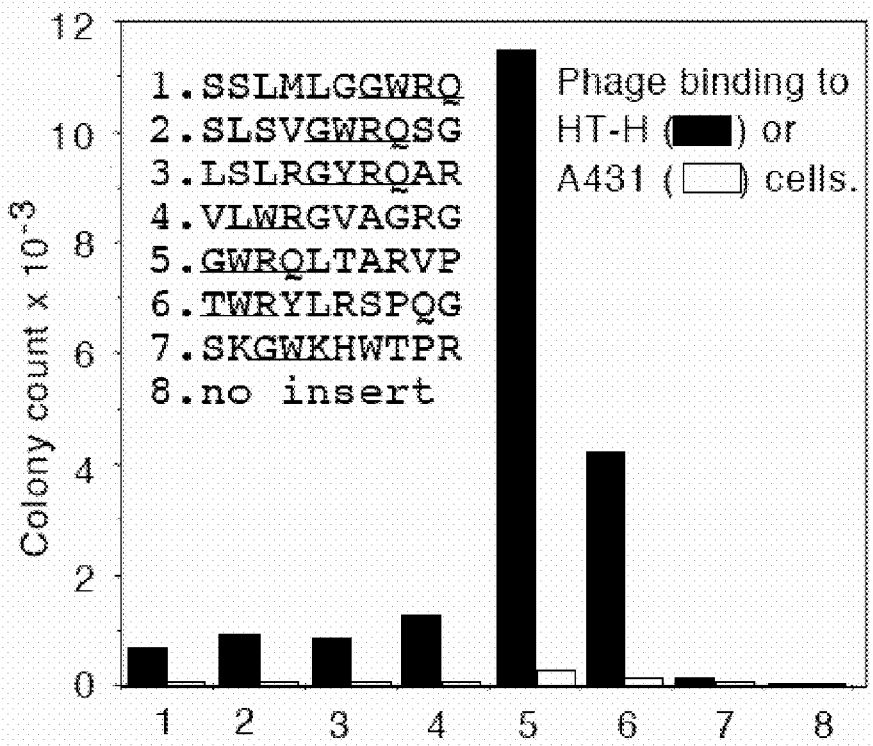
FIGS. 1A-C show phage binding on HT-H cells and control A431 cells. Screening a 9-mer peptide phage library identified a series of peptides ("GWRQ" peptides) with the consensus sequence GWRQ (SEQ ID NO:2). These are SEQ ID NOs:19 to 25, respectively. Note that strong binders display the GWRQ (SEQ ID NO:2) sequence at the amino terminus (A). Shown is the effect of antibodies on GWRQ phage binding (B) or synthetic GWRQ peptide binding (C) to HT-H cells (lane 1) without antibody; (lane 2) with control antibody (anti-alkaline phosphatase); (lane 3) with anti-trophinin antibody.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a polypeptide is disclosed and discussed and a number of modifications that can be made to a number of molecules including the polypeptide are discussed, each and every combination and permutation of polypeptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. COMPOSITIONS

1. Trophinin-Binding Peptides

Disclosed are isolated polypeptides and peptides comprising trophinin-binding peptides. Trophinin-binding peptides generally comprise at least one segment that selectively binds trophinin. Such segments can be referred to as "trophinin-binding segments." In some aspects, the isolated polypeptide can bind to trophinin, such as to the extracellular domain of trophinin. As disclosed herein, trophinin and bystin complex with and arrest epidermal growth factor (EGF) receptor. Thus, in some aspects, the isolated polypeptide can inhibit the binding of trophinin to bystin and thus bystin-mediated arrest of epidermal growth factor (EGF) receptor. Further, in some aspect, the isolated polypeptide can promote EGF receptor autophosphorylation. The disclosed polypeptides and peptides comprising trophinin-binding peptides can have a variety of lengths and structures as described herein. Generally, the lengths can range from peptide to polypeptide length, and all such lengths are encompassed as described herein. Merely for the sake of convenience, the disclosed peptides and polypeptides generally are referred to herein as "polypeptides" but it is intended that use of this term encompasses such compositions that could be considered peptides, unless the context clearly indicates otherwise.

Generally, a first molecule, such as the disclosed peptides, that selectively binds a second molecule has a binding affinity greater than about $10^5$ (e.g., $10^6$, $10^7$, $10^8$, $10^9$, $10^{10}$, $10^{11}$, and $10^{12}$ or more) moles/liter for that second molecule.

In some aspects, each trophinin-binding segment independently consist essentially of from about 4 to about 50 amino acids, including about 4, 5, 6, 7, 8, 9, 10, 11, 12, 13, 14, 15, 16, 17, 18, 19, 20, 25, 30, 35, 40, 45, or 50 amino acids. The trophinin-binding segment can comprise less than about 100 amino acid residues, including less than about 100, 95, 90, 85, 80, 75, 70, 65, 60, 55, 50, 45, 40, 35, 30, 25, 20 amino acid residues. The trophinin-binding segment can comprise more than about 8 amino acid residues, including more than about 8, 9, 10, 11, 12, 13, 14, 15, 16, 17, 18, 19, 20, 25, 30, 35, 40, 45, or 50 amino acid residues.

In some aspects, each isolated peptide independently consist essentially of from about 4 to about 50 amino acids, including about 4, 5, 6, 7, 8, 9, 10, 11, 12, 13, 14, 15, 16, 17, 18, 19, 20, 25, 30, 35, 40, 45, or 50 amino acids. The isolated peptide can comprise less than about 100 amino acid residues, including less than about 100, 95, 90, 85, 80, 75, 70, 65, 60, 55, 50, 45, 40, 35, 30, 25, 20 amino acid residues. The isolated peptide can comprise more than about 8 amino acid residues, including more than about 8, 9, 10, 11, 12, 13, 14, 15, 16, 17, 18, 19, 20, 25, 30, 35, 40, 45, or 50 amino acid residues.

In some aspects, the trophinin-binding peptide comprises the consensus sequence GWRQ (SEQ ID NO:2). In some aspects, the trophinin-binding peptide comprises a conservative variant of the consensus sequence. In some aspects, the trophinin-binding peptide comprises any three of the four amino acids in the consensus sequence GWRQ (SEQ ID NO:2). In some aspects, the trophinin-binding peptide comprises any three of the four amino acids in the consensus sequence GWRQ (SEQ ID NO:2) with the variant amino acid being G, A, L, I, T, or S if the first amino acid is variant; W or Y if the second amino acid is variant, R, K, or H if the third amino acid is variant, and Q, N, G, Y or H if the fourth amino acid is variant. In some aspects, the trophinin-binding peptide comprises any three of the four amino acids in the consensus sequence GWRQ (SEQ ID NO:2) with the variant amino acid being G, A, L, I, T, or S if the first amino acid is variant; W or Y if the second amino acid is variant, R, K, or H if the third amino acid is variant, and Q or N if the fourth amino acid is variant.

Also provided herein is an isolated polypeptide comprising one or more trophinin-binding segments, wherein the trophinin-binding segments each comprise the amino acid sequence $X_1X_2X_3X_4$ (SEQ ID NO:1), wherein
 $X_1$ is G, A, L, I, T, or S;
 $X_2$ is W or Y;
 $X_3$ is R, K, or H; and
 $X_4$ is Q, N, G, Y or H.

Also provided herein is an isolated polypeptide comprising one or more trophinin-binding segments, wherein the trophinin-binding segments each comprise the amino acid sequence $X_1X_2X_3X_4$ (SEQ ID NO:1), wherein
 $X_1$ is G, A, L, I, T, or S;
 $X_2$ is W or Y;
 $X_3$ is R, K, or H; and
 $X_4$ is Q or N.

As another example, the trophinin-binding segments can each comprise the amino acid sequence $X_1X_2X_3X_4X_5$ (SEQ ID NO:3), wherein
 $X_1$ is G, A, L, I, T, or S;
 $X_2$ is W or Y;
 $X_3$ is R, K, or H;
 $X_4$ is Q or N; and
 $X_5$ is S, A, V, or L.

As another example, the trophinin-binding segments can each comprise the amino acid sequence SSLMLGGWRQ (SEQ ID NO:19).

As another example, the trophinin-binding segments can each comprise the amino acid sequence GWRQ (SEQ ID NO:2), SLSVGWRQSG (SEQ ID NO:20), LSLRGYRQAR (SEQ ID NO:21), VLWRGVAGRG (SEQ ID NO:22), GWRQLTARVP (SEQ ID NO:23), TWRYLRSPQG (SEQ ID NO:24), SKGWKHWTPR (SEQ ID NO:25), or GWRQLTARVP SEQ ID NO:4).

Thus, at least one of the trophinin-binding segments can comprise the amino acid sequence GWRQ (SEQ ID NO:2), SLSVGWRQSG (SEQ ID NO:20), LSLRGYRQAR (SEQ ID NO:21), VLWRGVAGRG (SEQ ID NO:22), GWRQLTARVP (SEQ ID NO:23), TWRYLRSPQG (SEQ ID NO:24), SKGWKHWTPR (SEQ ID NO:25), or GWRQLTARVP SEQ ID NO:4). Thus, at least one of the trophinin-binding segments can consist essentially of the amino acid sequence GWRQ (SEQ ID NO:2), SLSVGWRQSG (SEQ ID NO:20), LSLRGYRQAR (SEQ ID NO:21), VLWRGVAGRG (SEQ ID NO:22), GWRQLTARVP (SEQ ID NO:23), TWRYLRSPQG (SEQ ID NO:24), SKGWKHWTPR (SEQ ID NO:25), or GWRQLTARVP SEQ ID NO:4), or a conservative variant or fragment of at least 6, 7, 8, 9, or 10 amino acids in length.

It is understood that any of the herein disclosed compositions, including peptides, and nucleic acids encoding the peptides, can be used in combination with any of the herein disclosed compositions and methods. For example, where a peptide is described, and fragments of that peptide are described, the disclosure of a method of using the peptide is also a disclosure of a method of using any of the disclosed fragments of that peptide. Also contemplated are compositions and methods comprising combinations of any two or more of the disclosed peptides and/or nucleic acids.

2. MAPS

In order to increase efficiency, the disclosed isolated polypeptide can be polymeric. For example, Multiple Antigen Peptide System (MAPS), first described by Dr. James Tam as a method of presenting epitopes to the immune system, is based on a small immunologically inert core molecule of radially branching lysine dendrites onto which a number of peptide antigens are anchored. The result is a large macromolecule which has a high molar ratio of peptide antigen to core molecule and does not require further conjugation to a carrier protein.

Thus, the isolated polypeptide can comprise two or more trophinin-binding segments, including 2, 3, 4, 5, 6, 7, 8, 9, 10, 11, 12, 13, 14, 15 or more segments. In some aspects, the isolated polypeptide can comprise eight trophinin-binding segments. In some aspects, the isolated polypeptide is unbranched, wherein two or more segments are on the same linear polypeptide. In other aspects, the isolated polypeptide comprises two or more amino acid branches, including 2, 3, 4, 5, 6, 7, 8, 9, 10, 11, 12, 13, 14, 15 or more amino acid branches. Thus, the isolated polypeptide can comprise a peptidyl core of 2, 3, 4, 5, 6, 7, 8, 9, 10 or more branched lysine residues, wherein two or more of the trophinin-binding segments are linked to two or more branched lysine residues. In addition, each of the branches can be monomeric or polymeric. The trophinin-binding segments in polymeric peptides can be the same or any mixture of the disclosed trophinin-binding segments. For example, each trophinin-binding segment can be independently selected.

For example, disclosed herein is a composition comprising 2, 3, 4, 5, 6, 7, 8, 9, 10, 11, 12, 13, 14, 15, 16, 17, 18, 19, 20 trophinin-binding segments linked to peptidyl core of 2, 3, 4, 5, 6, 7, 8, 9, 10 or more branched lysine residues. As used herein "GWRQ-MAP" or "GWRQ-MAPS" refers to a composition comprising 2, 3, 4, 5, 6, 7, 8, 9, 10, 11, 12, 13, 14, 15, 16, 17, 18, 19, 20 peptides comprising GWRQ (SEQ ID NO:2) linked to apeptidyl core of 2, 3, 4, 5, 6, 7, 8, 9, 10 or more branched lysine residues.

In some aspects, at least one trophinin-binding segment is less than about 0 to about 20 amino acids from the amino terminus of the polypeptide, including about 0, 1, 2, 3, 4, 5, 6, 7, 8, 9, 10, 11, 12, 13, 14, 15, 16, 17, 18, 19, or 20 amino acids from the amino terminus.

The disclosed polypeptides can be artificial sequences and can be synthesized in vitro and/or recombinantly. The disclosed polypeptides can be peptides that are not naturally occurring proteins and can be peptides that have at least two contiguous sequences that are not contiguous in a naturally occurring protein. The disclosed polypeptides can be 5 to about 50 amino acids in length. The disclosed polypeptides can be less than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 amino acids in length.

3. Internalization Sequence

The provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 1).

TABLE 1

Cell Internalization Transporters

| Name | Sequence | SEQ ID NO |
| --- | --- | --- |
| Antp | RQPKIWFPNRRKPWKK | (SEQ ID NO: 26) |
| HIV-Tat | GRKKRRQRPPQ | (SEQ ID NO: 27) |
| Penetratin | RQIKIWFQNRRMKWKK | (SEQ ID NO: 28) |
| Antp-3A | RQIAIWFQNRRMKWAA | (SEQ ID NO: 29) |
| Tat | RKKRRQRRR | (SEQ ID NO: 30) |
| Buforin II | TRSSRAGLQFPVGRVHRLLRK | (SEQ ID NO: 31) |
| Transportan | GWTLNSAGYLLGKINKALAALAKKIL | (SEQ ID NO: 32) |
| model amphipathic peptide (MAP) | KLALKLALKALKAALKLA | (SEQ ID NO: 33) |
| K-FGF | AAVALLPAVLLALLAP | (SEQ ID NO: 34) |
| Ku70 | VPMLK- PMLKE | (SEQ ID NO35) |
| Prion | MANLGYWLLALFVTMWTDVGLCKKRPKP | (SEQ ID NO: 36) |
| pVEC | LLIILRRRIRKQAHAHSK | (SEQ ID NO: 37) |
| Pep-1 | KETWWETWWTEWSQPKKKRKV | (SEQ ID NO: 38) |
| SynB1 | RGGRLSYSRRRFSTSTGR | (SEQ ID NO: 39) |
| Pep-7 | SDLWEMMMVSLACQY | (SEQ ID NO: 40) |
| HN-1 | TSPLNIHNGQKL | (SEQ ID NO: 41) |
| BGSC (Bis-Guanidinium-Spermidine-Cholesterol) | | |

BGSC

TABLE 1-continued

Cell Internalization Transporters

| Name | Sequence | SEQ ID NO |
|---|---|---|
| BGTC (Bis-Guanidinium-Tren-Cholesterol) | 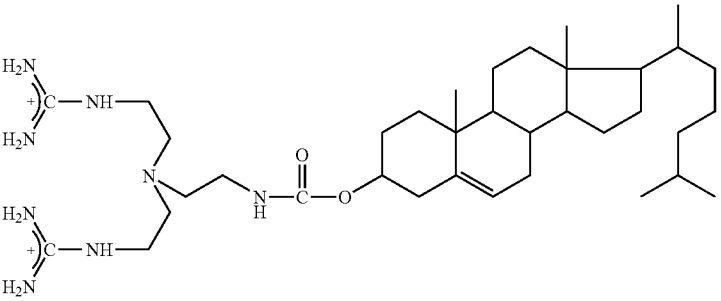<br>BGTC | |

Thus, the provided polypeptide can further comprise the amino acid sequence SEQ ID NO:26, SEQ ID NO:27 (Bucci, M. et al. 2000. Nat. Med. 6, 1362-1367), SEQ ID NO:28 (Derossi, D., et al. 1994. Biol. Chem. 269, 10444-10450), SEQ ID NO:29 (Fischer, P. M. et al. 2000. J. Pept. Res. 55, 163-172), SEQ ID NO:30 (Frankel, A. D. & Pabo, C. O. 1988. Cell 55, 1189-1193; Green, M. & Loewenstein, P. M. 1988. Cell 55, 1179-1188), SEQ ID NO:31 (Park, C. B., et al. 2000. Proc. Natl. Acad. Sci. USA 97, 8245-8250), SEQ ID NO:32 (Pooga, M., et al. 1998. FASEB J. 12, 67-77), SEQ ID NO:33 (Oehlke, J. et al. 1998. Biochim. Biophys. Acta. 1414, 127-139), SEQ ID NO:34 (Lin, Y. Z., et al. 1995. J. Biol. Chem. 270, 14255-14258), SEQ ID NO:35 (Sawada, M., et al. 2003. Nature Cell Biol. 5, 352-357), SEQ ID NO:36 (Lundberg, P. et al. 2002. Biochem. Biophys. Res. Commun. 299, 85-90), SEQ ID NO:37 (Elmquist, A., et al. 2001. Exp. Cell Res. 269, 237-244), SEQ ID NO:38 (Morris, M. C., et al. 2001. Nature Biotechnol. 19, 1173-1176), SEQ ID NO:39 (Rousselle, C. et al. 2000. Mol. Pharmacol. 57, 679-686), SEQ ID NO:40 (Gao, C. et al. 2002. Bioorg. Med. Chem. 10, 4057-4065), or SEQ ID NO:41 (Hong, F. D. & Clayman, G. L. 2000. Cancer Res. 60, 6551-6556). The provided polypeptide can further comprise BGSC (Bis-Guanidinium-Spermidine-Cholesterol) or BGTC (Bis-Guanidinium-Tren-Cholesterol) (Vigneron, J. P. et al. 1998. Proc. Natl. Acad. Sci. USA. 93, 9682-9686). The preceding references are hereby incorporated herein by reference in their entirety for the teachings of cellular internalization vectors and sequences. Any other internalization sequences now known or later identified can be combined with a polypeptide disclosed herein.

4. Enzyme

Because the sperm tail is covered by carbohydrates including polysialic acids, removal of these carbohydrate enzymatically by enzymes can be used to further enhance the sperm motility. Thus, disclosed herein is a composition comprising a trophinin-binding peptide and an enzyme that degrades carbohydrates. For example, disclosed herein is a composition comprising a trophinin-binding peptide and an endo-neuraminidase. Also disclosed herein is a composition comprising a trophinin-binding peptide and an endo-beta-galactosidase. Also disclosed herein is a composition comprising a trophinin-binding peptide and an N-glycanase.

5. Nucleic Acids

Also provided herein is an isolated nucleic acid encoding a polypeptide comprising one or more trophinin-binding segments. The encoded polypeptides and trophinin-binding segments can be any of the disclosed polypeptides or trophinin-binding segments. For example, provided herein is an isolated nucleic acid encoding a polypeptide comprising one or more trophinin-binding segments, wherein at least one trophinin-binding segment comprises the amino acid sequence $X_1X_2X_3X_4$ (SEQ ID NO:1), wherein $X_1$ is G, A, L, I, T, or S;
$X_2$ is W or Y;
$X_3$ is R, K, or H; and
$X_4$ is Q or N.

As another example, provided herein is an isolated nucleic acid encoding a polypeptide comprising one or more trophinin-binding segments, wherein at least one trophinin-binding segment comprises the amino acid sequence $X_1X_2X_3X_4X_5$ (SEQ ID NO:3), wherein $X_1$ is G, A, L, I, T, or S;
$X_2$ is W or Y;
$X_3$ is R, K, or H;
$X_4$ is Q or N; and
$X_5$ is S, A, V, or L.

As another example, provided herein is an isolated nucleic acid encoding a polypeptide comprising one or more trophinin-binding segments, wherein at least one trophinin-binding segment comprises the amino acid sequence GWRQ (SEQ ID NO:2). Also provided herein is an isolated nucleic acid encoding a polypeptide comprising one or more trophinin-binding segments, wherein at least one trophinin-binding segment comprises the amino acid sequence SSLMLGGWRQ (SEQ ID NO:19), SLSVGWRQSG (SEQ ID NO:20), LSL-RGYRQAR (SEQ ID NO:21), VLWRGVAGRG (SEQ ID NO:22), GWRQLTARVP (SEQ ID NO:23), TWRYLR-SPQG (SEQ ID NO:24), SKGWKHWTPR (SEQ ID NO:25), or GWRQLTARVP (SEQ ID NO:4).

i. Nucleotides and Related Molecules

The disclosed nucleic acids can be made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

6. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

7. Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

8. Cell Delivery Systems

Also provided is a vector comprising a nucleic acid encoding a polypeptide disclosed herein, wherein the nucleic acid is operably linked to an expression control sequence. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

i. Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acid into the cell without degradation and include a promoter yielding expression of the gene in the cells into which it is delivered. Viral vectors include, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also disclosed are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Disclosed is a viral vector that has been engineered to suppress the immune response of the host organism, elicited by the viral antigens. Example vectors of this type can carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

d. Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

ii. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Felgner et al. Proc. Natl. Acad. Sci. USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (InaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

iii. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

9. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

i. Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

ii. Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

10. Polypeptides and Peptides i. Protein Variants

Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table and 2 and are referred to as conservative substitutions.

TABLE 2

Amino Acid Substitutions
Original Residue Exemplary Conservative
Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Specifically disclosed are variants of these and other polypeptides herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH) $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH—$H_2$—S); Hann J. Chem. Soc Perkin Trans. 1307-314 (1982) (—CH—CH—, cis and trans); Ahnquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C (OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

11. Antibodies

Also disclosed herein are antibodies that specifically bind any of the polypeptides disclosed herein. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with a polypeptides disclosed herein.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes can be immunized in vitro, e.g., using the HIV Env-CD4-co-receptor complexes described herein.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

12. Pharmaceutical Carriers

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

B. METHODS

The disclosed polypeptides and nucleic acids can be used for a variety of purposes. In particular, the disclosed polypeptides can be used to affect cells and treat conditions and diseases generally based on the binding ability of the polypeptides. Any of the disclosed polypeptides can be used in these methods. For example, polypeptides comprising a peptidyl core of 2, 3, 4, 5, 6, 7, 8, 9, 10 or more branched lysine residues, wherein two or more of the trophinin-binding segments are linked to two or more branched lysine residues can be used in the disclosed methods.

For example, the trophinin-binding segment can comprise the amino acid sequence $X_1X_2X_3X_4$ (SEQ ID NO:1), wherein
 $X_1$ is G, A, L, I, T, or S;
 $X_2$ is W or Y;
 $X_3$ is R, K, or H; and
 $X_4$ is Q or N.

For example, the trophinin-binding segment can comprise the amino acid sequence $X_1X_2X_3X_4X_5$ (SEQ ID NO:3), wherein
 $X_1$ is G, A, L, I, T, or S;
 $X_2$ is W or Y;
 $X_3$ is R, K, or H;
 $X_4$ is Q or N; and
 $X_5$ is S, A, V, or L.

For example, the trophinin-binding segment can comprise the amino acid sequence GWRQ (SEQ ID NO:2). For example, the trophinin-binding segment can comprise the amino acid sequence SSLMLGGWRQ (SEQ ID NO:19).

For example, the trophinin-binding segment can comprise the amino acid sequence SLSVGWRQSG (SEQ ID NO:20).

For example, the trophinin-binding segment can comprise the amino acid sequence LSLRGYRQAR (SEQ ID NO:21).

For example, the trophinin-binding segment can comprise the amino acid sequence VLWRGVAGRG (SEQ ID NO:22).

For example, the trophinin-binding segment can comprise the amino acid sequence GWRQLTARVP (SEQ ID NO:23).

For example, the trophinin-binding segment can comprise the amino acid sequence TWRYLRSPQG (SEQ ID NO:24).

For example, the trophinin-binding segment can comprise the amino acid sequence SKGWKHWTPR (SEQ ID NO:25).

For example, the trophinin-binding segment can comprise the amino acid sequence GWRQLTARVP (SEQ ID NO:4).

Particularly useful are concentrations of from about 2-20 μg/ml of the polypeptide. Particularly useful are polypeptides comprising eight trophinin-binding segments.

1. Promoting Cell Growth

Provided is a method of promoting the growth of a trophoblastic cell, comprising contacting the cell with a polypeptide comprising one or more trophinin-binding segments disclosed herein. Also provided is a method of promoting the activation of a trophoblastic cell, comprising contacting a blastocyst or trophectoderm with a polypeptide comprising one or more trophinin-binding segments disclosed herein. Any of the disclosed polypeptides can be used in these methods, including any of the disclosed branched polypeptides. For example, polypeptides comprising a peptidyl core of 2, 3, 4, 5, 6, 7, 8, 9, or more branched lysine residues, wherein two or more of the trophinin-binding segments are linked to two or more branched lysine residues can be used in the disclosed methods.

2. Promoting Stem Cell Formation

Also provided is a method of promoting the formation of a pluripotent stem cell, comprising contacting a blastocyst cell, morula cell, epiblast cell, or primordial germ cell with a polypeptide comprising one or more trophinin-binding segments disclosed herein. Any of the disclosed polypeptides can be used in these methods, including any of the disclosed branched polypeptides. For example, polypeptides comprising a peptidyl core of 2, 3, 4, 5, 6, 7, 8, 9, 10 or more branched lysine residues, wherein two or more of the trophinin-binding segments are linked to two or more branched lysine residues can be used in the disclosed methods.

One category of stem cells is a blastocyst-derived stem cell which is a pluripotent stem cell which was derived from a cell which was obtained from a blastocyst prior to the, for example, 64, 100, or 150 cell stage. Blastocyst-derived stem cells can be derived from the inner cell mass of the blastocyst and are the cells commonly used in transgenic mouse work (Evans and Kaufman, (1981) Nature 292:154-156; Martin, (1981) Proc. Natl. Acad. Sci. 78:7634-7638). Blastocyst-derived stem cells isolated from cultured blastocysts can give rise to permanent cell lines that retain their undifferentiated characteristics indefinitely. Blastocyst-derived stem cells can be manipulated using any of the techniques of modern molecular biology, then re-implanted in a new blastocyst. This blastocyst can give rise to a full term animal carrying the genetic constitution of the blastocyst-derived stem cell. (Misra and Duncan, (2002) Endocrine 19:229-238). Such properties and manipulations are generally applicable to blastocyst-derived stem cells. It is understood blastocyst-derived stem cells can be obtained from pre or post implantation embryos and can be referred to as that there can be pre-implantation blastocyst-derived stem cells and post-implantation blastocyst-derived stem cells respectively.

Another category of stem cells are embryo derived stem cells which are derived from embryos of 150 cells or more up to 6 weeks of gestation. Typically embryo derived stem cells will be derived from cells that arose from the inner cell mass cells of the blastocyst or cells which will be come gonadal ridge cells, which can arise from the inner cell mass cells, such as cells which migrate to the gonadal ridge during development. Another category of stem cells are Morula derived stem cells which are stem cells derived from a Morula stage embryo. Other sets of stem cells are embryonic stem cells, (ES cells), embryonic germ cells (EG cells), and embryonic carcinoma cells (EC cells).

Stem cells can also be classified by their potential for development. One category of stem cells are stem cells that can grow into an entire organism. Another category of stem cells are stem cells (which have pluripotent capabilities as defined above) that cannot grow into a whole organism, but can become any other type of cell in the body. Another category of stem cells are stem cells that can only become particular types of cells: e.g. blood cells, or bone cells. Other categories of stem cells include totipotent, pluripotent, and multipotent stem cells.

Stem cells can be cultured using any culture means which promotes the properties of the desired type of stem cell. See U.S. Pat. Nos. 5,690,926; 5,670,372, and 5,453,357, which are all incorporated herein by reference for material at least related to deriving and maintaining pluripotential embryonic stem cells in culture. Stem cells can also be cultured on feeder cells, e.g. embryonic fibroblasts, and dissociated cells can be re-plated on embryonic feeder cells. See for example, U.S. Pat. Nos. 6,200,806 and 5,843,780 which are herein incorporated by reference at least for material related to deriving and maintaining stem cells. Stem cells can also be cultured on a solid substrate, e.g. plastic, glass or the like, absent a feeder layer and/or conditioned media.

Particularly useful are concentrations of from about 2-20 μg/ml of the polypeptide. Particularly useful are polypeptides comprising eight trophinin-binding segments.

3. Promoting Neuronal Growth and Treating Nueral Disease or Injury

As disclosed herein, trophinin-binding peptides promote neuronal growth in vitro or in vivo. Thus, also provided is a method of promoting growth of a neuron, comprising administering to the neuron a composition comprising a polypeptide comprising one or more trophinin-binding segments disclosed herein or a nucleic acid encoding same. Any of the disclosed polypeptides can be used in these methods, including any of the disclosed branched polypeptides. For example, polypeptides comprising a peptidyl core of 2, 3, 4, 5, 6, 7, 8, 9, 10 or more branched lysine residues, wherein two or more of the trophinin-binding segments are linked to two or more branched lysine residues can be used in the disclosed methods.

Thus, trophinin-binding peptides can further be used to treat any condition or disease wherein neuronal growth is desired. Thus, also provided is a method of treating a subject with neural injury or disease, comprising administering to the subject a composition comprising one or more trophinin-binding segments disclosed herein or a nucleic acid encoding same. For example, the neural injury or disease can be a stroke, spinal cord injury, peripheral nerve injury, traumatic brain injury, retinal degeneration, epilepsy, neuropsychiatric disorder, pain disorder, or neurodegenerative disorder. In aspects involving the use of a nucleic acid encoding a trophinin-binding peptide, the nucleic acid can be in a viral vector that can cross the blood-brain-barrier. Particularly useful are concentrations of from about 2-20 μg/ml of the polypeptide. Particularly useful are polypeptides comprising eight trophinin-binding segments.

4. Promoting Sperm Motility

Also provided is a method of promoting sperm motility, comprising contacting the sperm with a polypeptide comprising one or more trophinin-binding segments disclosed herein.

In some aspects, the disclosed method does not increase activated sperm motility.

In some aspects, the disclosed method increases hyperactivated sperm motility.

In some aspects, the disclosed method does not enhance a long distance, forward movement. In some aspects, the disclosed method does enhance short distance forward movement. In some aspects, short distance forward movement is increased by at least about 10%, 20%, 30%, 40%, 50%, or higher.

For example, the method can be used to improve fertilization during in vitro fertilization. In some aspects, fertilization can be increased by at least about 10%, 20%, 30%, 40%, 50%, or higher.

The disclosed method can also be used to increase sperm motility in a subject. Thus, disclosed is a method of promoting sperm motility in a subject in need thereof, comprising administering to the subject a polypeptide comprising one or more trophinin-binding segments disclosed herein.

In some aspects, the peptide is administered to enhance short distance movement after the sperm have already reached the fallopian tube. Thus, also disclosed is a method of promoting motility of sperm delivered via intercourse, comprising administering to the subject a polypeptide comprising one or more trophinin-binding segments disclosed herein about 0, 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, or more hours after intercourse.

Also disclosed is a method of promoting motility of sperm delivered via intercourse, comprising use of, for example, a personal lubricant comprising a polypeptide comprising one or more trophinin-binding segments disclosed herein. Thus, disclosed herein is a composition comprising a polypeptide comprising one or more trophinin-binding segments disclosed herein in a solution comprising polyhydric alcohols and/or water-soluble cellulose-derived polymers.

The polyhydric alcohol portion of the product can make up from about 5 to about 90% by weight of the composition. For example, the polyhydric alcohol portion of the composition is glycerin, propylene glycol and/or sorbitol.

The cellulose-derived polymers can be cellulose gum such as hydroxyethylcellulose, although other polyols known to those of ordinary skill in the art may be used, such as carboxymethylcellulose, hydroxypropylcellulose and hydroxypropylmethylcellulose and the like.

A combination of gums and one or more of the polyhydric alcohols can be used, with one element being present in a significantly greater amount (polyhydric alcohol) than the other (cellulose gum). For example, the polyhydric alcohol can be glycerin. For example, the gum can be hydroxyethylcellulose.

Any of the disclosed polypeptides can be used in these methods, including any of the disclosed branched polypeptides. For example, polypeptides comprising a peptidyl core of 2, 3, 4, 5, 6, 7, 8, 9, 10 or more branched lysine residues, wherein two or more of the trophinin-binding segments are linked to two or more branched lysine residues can be used in the disclosed methods.

Particularly useful are concentrations of from about 2-20 μg/ml of the polypeptide. Particularly useful are polypeptides comprising eight trophinin-binding segments.

5. Administration

Compositions disclosed herein, including the disclosed polypeptides and nucleic acids, can be administered in a number of ways depending on whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions can be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the trophinin-binding peptide used alone might range from about 1 μg/kg to up to 100 mg/kg of body weight or more per day, depending on the factors mentioned above. Particularly useful are concentrations of from about 2-20 μg/kg body weight of the polypeptide. Particularly useful are polypeptides comprising eight trophinin-binding segments.

Following administration of a disclosed composition for treating a neural injury, the efficacy of the therapeutic peptide can be assessed in various ways well known to the skilled practitioner. For instance, one of ordinary skill in the art will understand that a composition disclosed herein is efficacious in treating a neural injury in a subject by observing that the composition promotes growth of a neuron. Neuronal growth can be measured by methods that are known in the art. Efficacy of the administration of the disclosed composition can also be determined by evaluating cognitive function in the subject.

The compositions that inhibit trophinin/dystin interactions disclosed herein can be administered prophylactically to patients or subjects who are at risk for low sperm motility or who have been newly diagnosed with low sperm motility.

Other molecules that interact with disclosed peptides to inhibit trophinin/dystin interactions which do not have a specific pharmaceutical function, but which can be used for tracking changes within cellular chromosomes or for the delivery of diagnostic tools for example can be delivered in ways similar to those described for the pharmaceutical products.

C. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Disclosed are processes for making the compositions as well as making the intermediates leading to the compositions. For example, disclosed are nucleic acids in SEQ ID NOs:5 to 18. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO:5, 6, 7, 8, 9, 10, 11, 12, 13, 14, 15, 16, 17, or 18 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO:5, 6, 7, 8, 9, 10, 11, 12, 13, 14, 15, 16, 17, or 18 and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO:5, 6, 7, 8, 9, 10, 11, 12, 13, 14, 15, 16, 17, or 18 and a sequence controlling the expression of the nucleic acid.

Disclosed are nucleic acid molecules produced by the process comprising linking in an operative way a nucleic acid molecule comprising a sequence encoding a peptide set forth in SEQ ID NO:1, 2, 3, 4, 19, 20, 21, 22, 23, 24, or 25 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:1, 2, 3, 4, 19, 20, 21, 22, 23, 24, or 25 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO: 1, 2, 3, 4, 19, 20, 21, 22, 23, 24, or 25, wherein any change is a conservative change, and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

D. USES

The disclosed compositions can be used in a variety of ways as disclosed herein as well as research tools. For example, the disclosed compositions, such an isolated polypeptide comprising SEQ ID NOs: 1, 2, 3, or 4 can be used to study the interactions between trophinin and bystin, by for example acting as inhibitors of binding. Other uses are disclosed, apparent from the disclosure, and/or will be understood by those in the art.

E. DEFINITIONS

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "subject" means any target of administration. The subject can be a vertebrate, for example, a mammal. Thus, the subject can be a human. In some aspects, the subject is not human. Thus, the subject can be, for example, a mouse, rat, rabbit, cow, sheep, pig, or primate. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

F. EXAMPLES

1. Example 1

Trophinin-Mediated Cell Adhesion as a Molecular Switch for EGF Receptor Activation in Human Embryo Implantation i. Results The trophoblastic embryonal carcinoma HT-H line was used as a model for trophectoderm cells of the human blastocyst (Fukuda, M N, et al. 1999). The HT-H cells adhered with high affinity to the apical surface of trophinin-expressing endometrial adenocarcinoma cells. Morphological changes in the HT-H cells indicated that trophinin-mediated cell adhesion activated signaling in these cells. Indeed, the binding of suspended HT-H cells to an HT-H cell monolayer caused significant elevation of tyrosine phosphorylation (24.5±2.06% of positive cells vs. control 0.8±0.75%, n=5).

HT-H monolayer was incubated in medium containing $Na_3VO_4$, overlayed with (right) or without an HT-H cell suspension, and stimulated for phosphorylation at 37° C. for 30 min. Adhered HT-H cells were removed by gentle pipetting, and the HT-H monolayer was stained with anti-pY antibody to detect tyrosine phosphorylated proteins. HT-H cells reacted with goat anti-mouse IgM antibodies as a control or with mouse monoclonal anti-trophinin antibody directed to the extracellular domain of trophinin and followed by goat anti-mouse IgM second antibody. The cells were incubated at 37° C. for 30 min to induce phosphorylation and then stained with rhodamine-phalloidin for F-actin and an anti-phosphotyrosine antibody.

Trophinin-mediated cell adhesion is based on a unique structure created by trophinin clustered on the cell surface (Fukuda, M N, et al. 1995). To mimic trophinin-mediated cell adhesion, HT-H cells were reacted with a monoclonal antibody directed to the cell surface domain of trophinin (Suzuki, N. et al. 1999) and then cross-linked with a second antibody (Tada, J, et al. 1999). HT-H cells cross-linked with anti-trophinin antibody showed enhanced levels of F-actin formation and tyrosine phosphorylation, indicating that a conformational arrest of trophinin on the cell surface was transmitted to the cytoplasm.

Figure 1B:
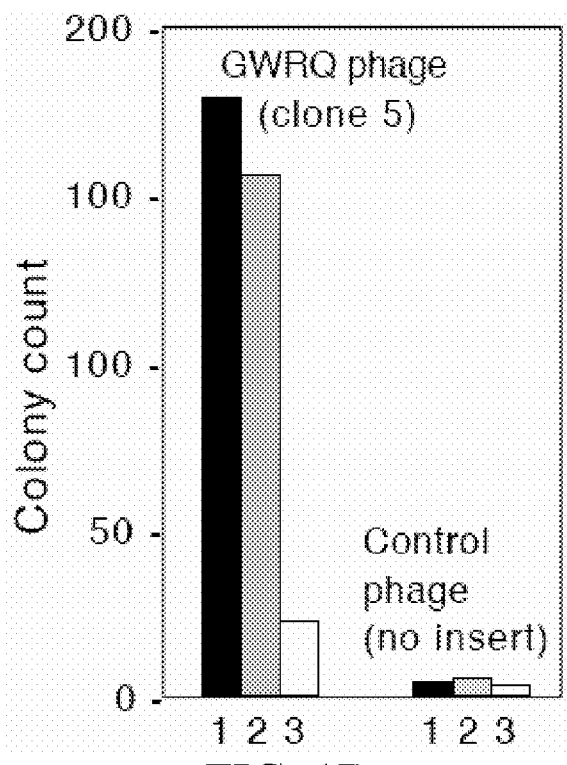
Figure 1C:
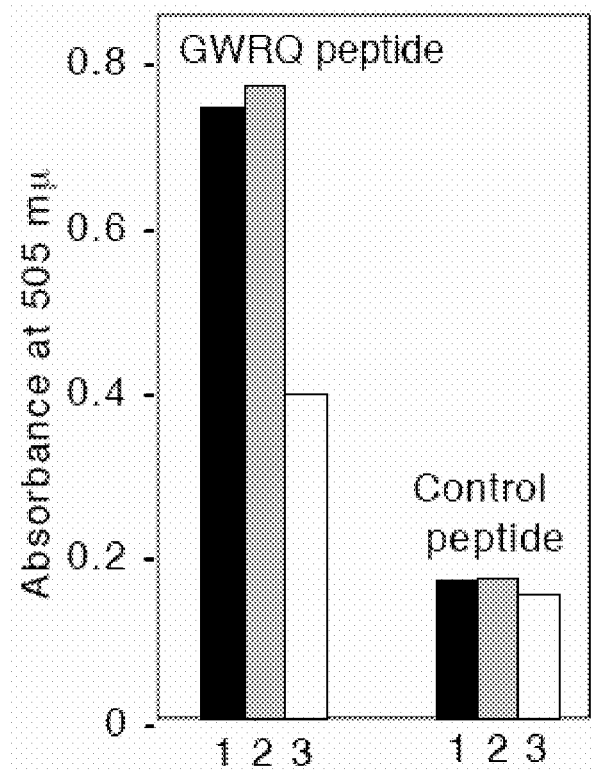
Figure 1D:
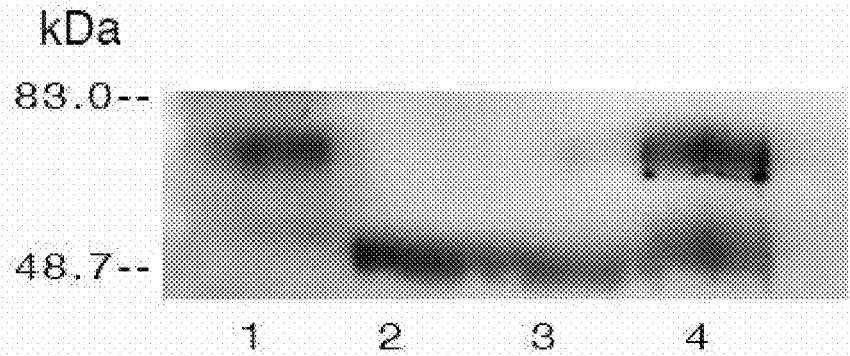
FIG. 1D shows Western blot with anti-trophinin antibody. Untreated HT-H cell lysate (lane 1). Lanes 2-4, immunoprecipitates from HT-H lysates obtained as follows: (lane 2) incubated with GWRQ phage, followed by immunoprecipitation with rabbit IgG; (lane 3) incubated with control phage, followed by immunoprecipitation with rabbit anti-phage antibody; (lane 4) incubated with GWRQ phage, followed by immunoprecipitation with anti-phage antibody.
Figure 1E:
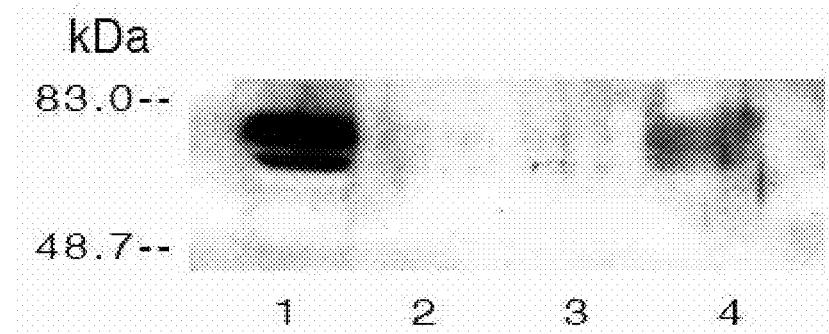
FIG. 1E shows Western blot with anti-trophinin antibody. Untreated HT-H cell lysate (lane 1). Lanes 2-4, pull-down products from HT-H lysates obtained as follows: lane 2 was incubated with biotinylated GWRQ peptide and collected by avidin beads; lane 3 was incubated with biotinylated control peptide and collected by avidin beads; lane 4 was incubated with biotinylated GWRQ peptide and collected by avidin beads.

It was next determined whether a small molecule fitting the binding pocket of trophinin would mimic trophinin-mediated cell adhesion. A peptide displaying phage library was screened using an HT-H cell monolayer as a target. This screening identified a series of peptides containing the consensus sequence GWRQ (SEQ ID NO:2) (FIG. 1A). These peptides are referred to herein as "GWRQ" peptides and are examples of the disclosed trophinin-binding peptides. Specificity of GWRQ for trophinin was ascertained in several ways. First, phage clones displaying the GWRQ peptide bound to HT-H cells, but not to control A431 cells. Second, anti-trophinin antibody inhibited binding of the GWRQ phage and of a synthetic GWRQ peptide to HT-H cells, whereas an irrelevant antibody had no effect (FIG. 1B,C). Third, when GWRQ phage was bound on the surface of HT-H cell surface and HT-H cell proteins were immunoprecipitated with anti-phage antibody, trophinin was detected in the immunoprecipitate (FIG. 1D). Finally, when biotinylated GWRQ peptide was bound on the surface of HT-H cells and HT-H cell proteins were precipitated with avidin beads, trophinin was detected in the beads-bound fraction (FIG. 1E). These results indicate that GWRQ peptide bound to the extracellular domain of trophinin.

When GWRQ peptide was added to HT-H cell cultures, actin polymerization and tyrosine phosphorylation were induced, whereas control peptides did not cause these effects. This indicates that the GWRQ peptide activated HT-H cells in a similar manner to the anti-trophinin antibody. As tyrosine phosphorylation and actin polymerization are indicators of cell motility, the effect of GWRQ was determined in motility assays. Both a wound-healing assay and an invasion assay showed that HT-H cells cultured with GWRQ were highly mobile compared to those cultured without. Furthermore, HT-H cells cultured in medium containing GWRQ were more proliferative than those cultured without (52.9±7.8% of cells positive for BrdU incorporation vs. 36.1±9.2%, n=6, p<0.05).

Figure 2A:
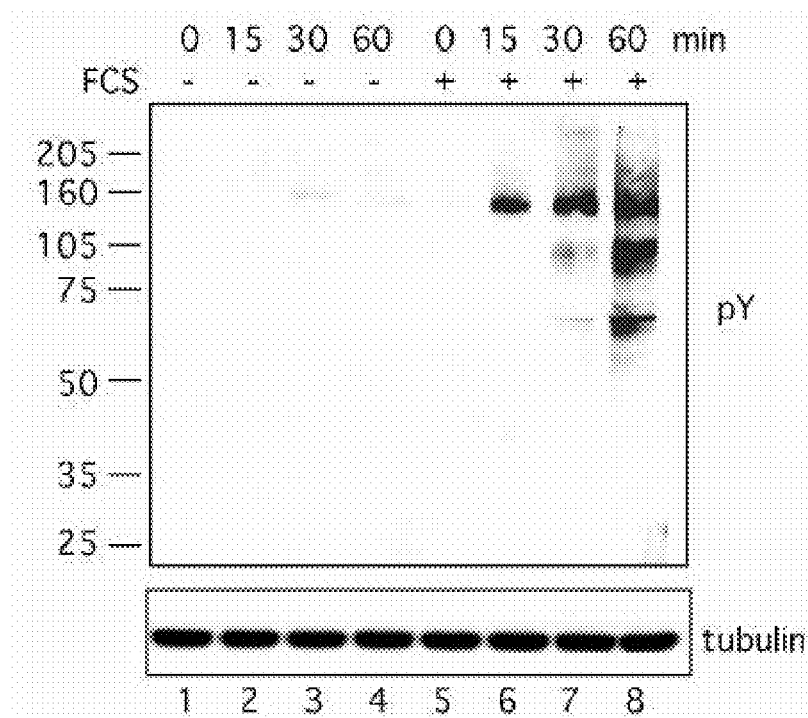
FIG. 2A shows Western blot for tyrosine phosphorylated proteins. HT-H cells were cultured in medium with or without fetal calf serum (FCS), treated with GWRQ peptide, and stimulated to induce phosphorylation for 0-60 min.

Since all these characteristics induced by GWRQ are hallmarks of cellular responses to growth factors present in fetal calf serum, the effect of GWRQ on HT-H cells cultured with or without fetal calf serum were compared. Western blot analysis revealed that, in the presence of serum, GWRQ increased levels of tyrosine-phosphorylated proteins. However, in the absence of serum, this did not occur (FIG. 2A), indicating that activation of HT-H by GWRQ is growth factor-dependent.

The major tyrosine-phosphorylated protein in the GWRQ-treated HT-H cells migrated at about 160 kDa. Immunoprecipitation and western blotting showed that this band represents EGF receptors, including ErbB4 (FIG. 2 and FIG. 3).

Figure 4:
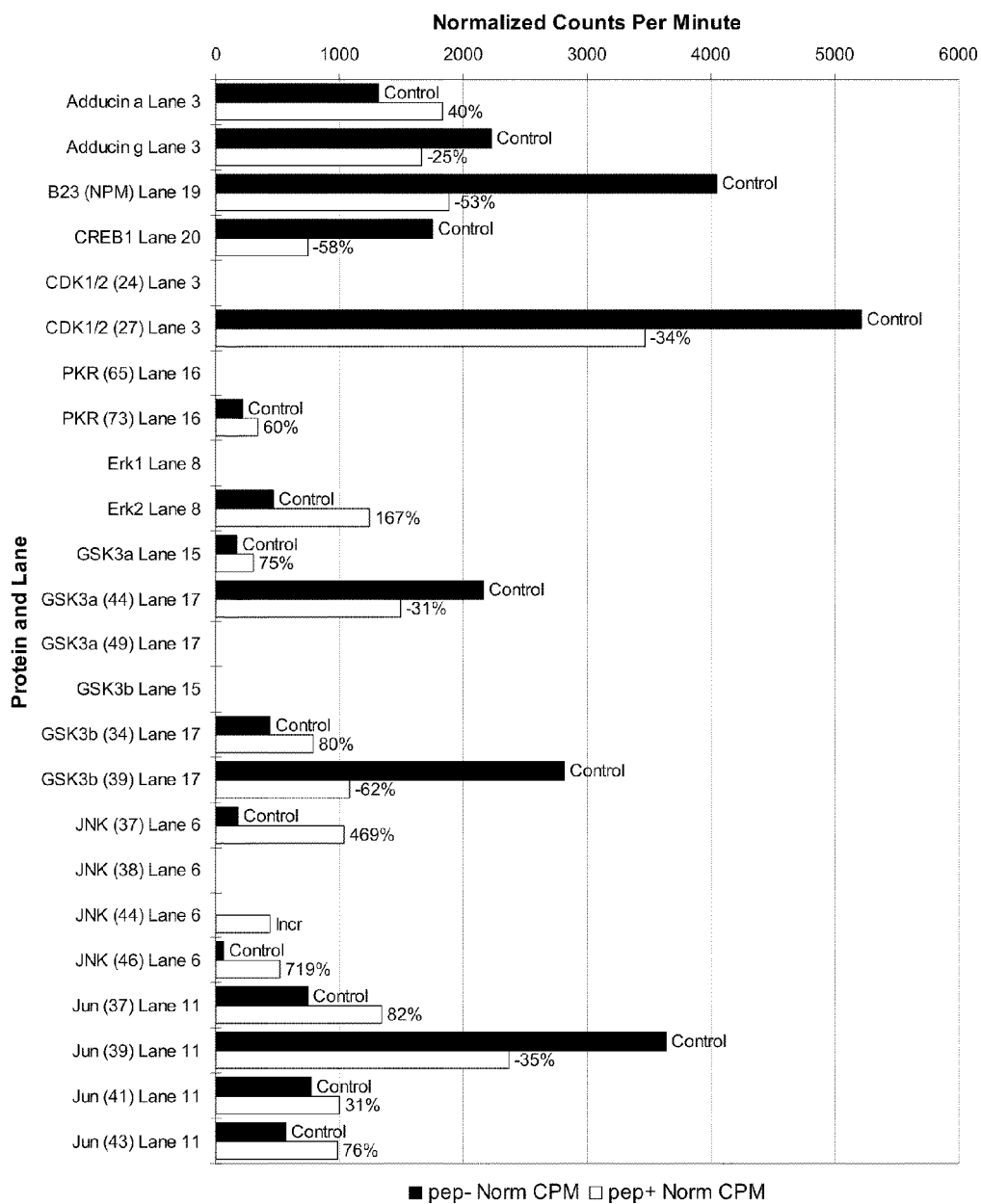
FIG. 4 shows summary of quantitative Western blot analysis of phosphorylated proteins in HT-H cells treated with or without GWRQ peptide. Western blot using phospho site-specific antibodies was used to quantify the level of phosphorylation of each protein. Epitope of each antibody is shown in parenthesis.
Figure 5:
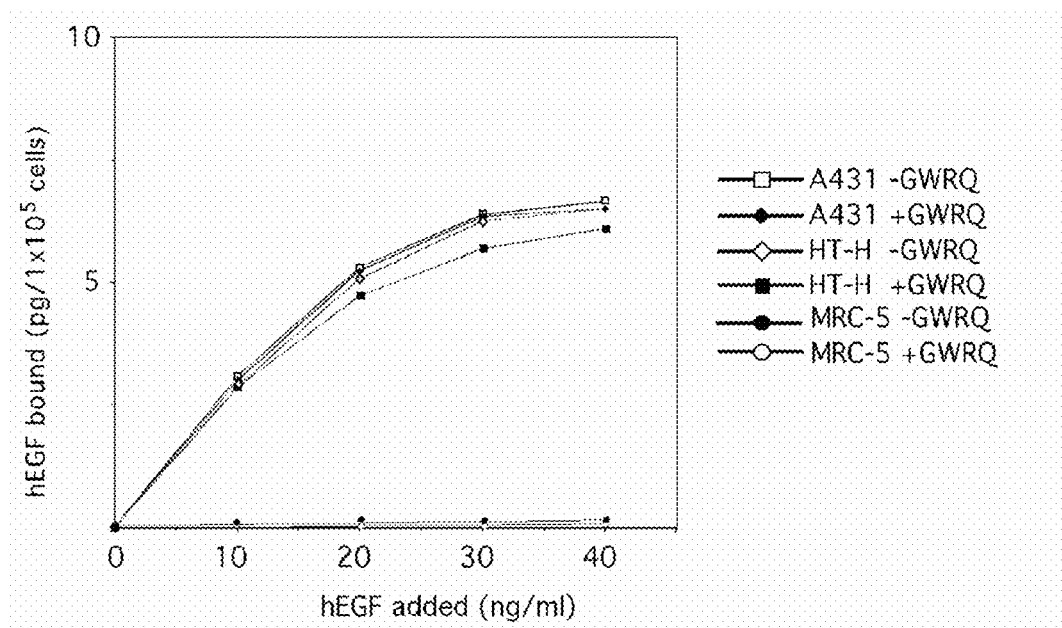
FIG. 5 shows binding of recombinant human EGF to HT-H cells, A431 cells and MRC-5 cells treated with or without GWRQ peptide. Data were obtained by duplicate measurements, of which the reading errors were less than 15%.

The GWRQ-dependent phosphorylation of EGFR indicates that GWRQ activates this signaling pathway (Blume-Jensen, P, et al. 2001; Carpenter, G. 2000). EGFR downstream proteins such as MAPK(p38), MEK3/6, S6K (p70), JNK, STAT3, Rb, and Src were phosphorylated in GWRQ-treated HT-H cells (FIG. 4), further indicating that the active component in serum needed for GWRQ activity was EGF. It was therefore examined whether GWRQ affected the binding of the EGF to HT-H cells, but no such effect was found (FIG. 5).

Figure 2B:
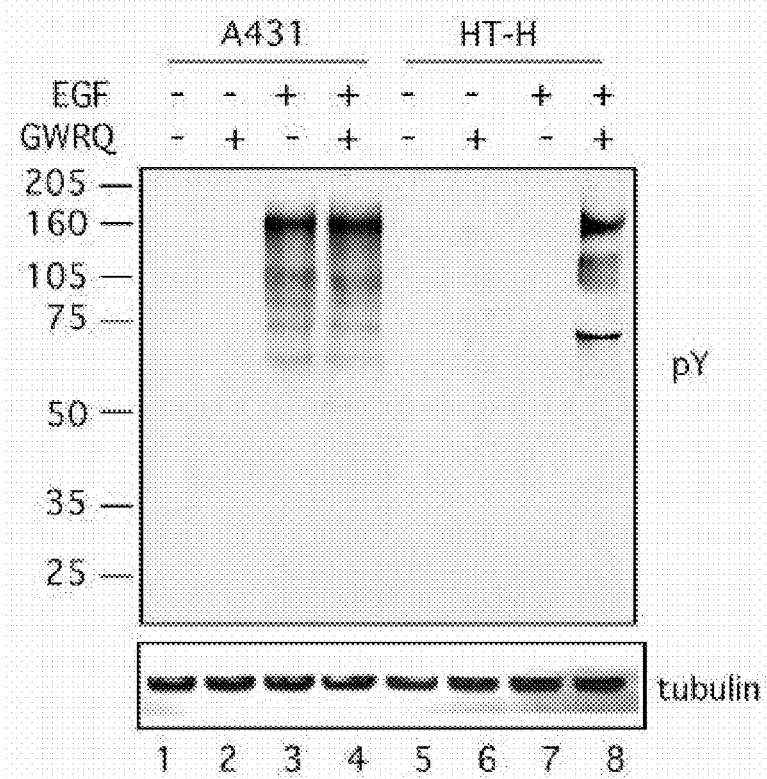
FIG. 2B shows Western blot for tyrosine phosphorylated proteins. A431 cells and HT-H cells were cultured with or without serum, treated with EGF and/or GWRQ peptide, and stimulated to induce phosphorylation for 30 min. Control peptides (Tada, J, et al. 1999) showed no effect on these cells.
Figure 3A:
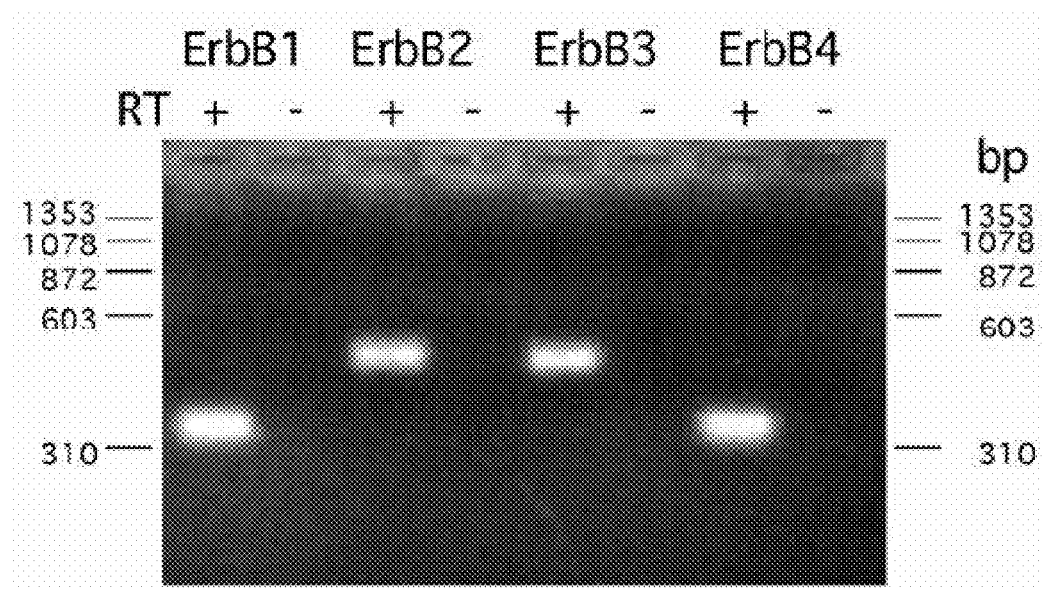
FIG. 3A shows RT-PCR for ErbB 1, 2, 3 and 4 transcripts from HT-H cells. Expected size for the PCR product for ErbB1, ErbB2, ErbB3, and ErbB4 are 303 bp, 380 bp, 378 bp, and 304 bp, respectively.
Figure 3B:
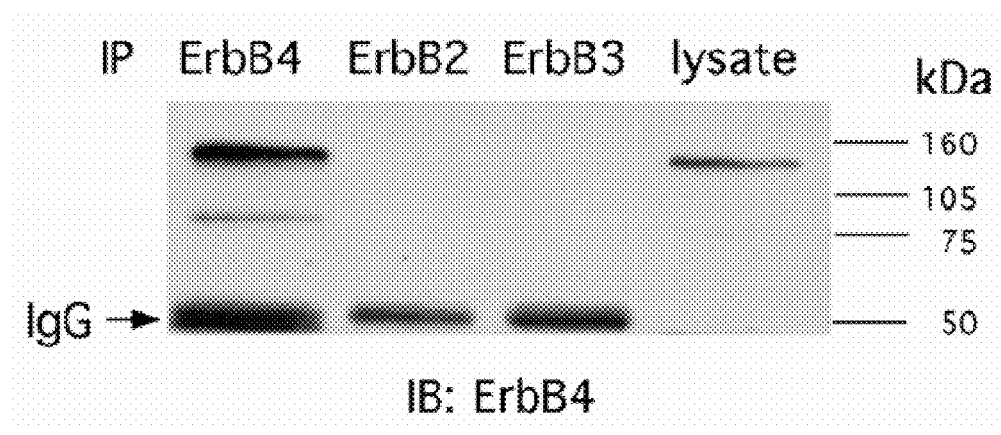
FIG. 3B shows Western blot analysis for ErbB4 protein expressed in HT-H cells. Each immunoprecipitate shown in the figure and total HT-H cell lysate were subjected to immunoblot with anti-ErbB4 antibody.
Figure 3C:
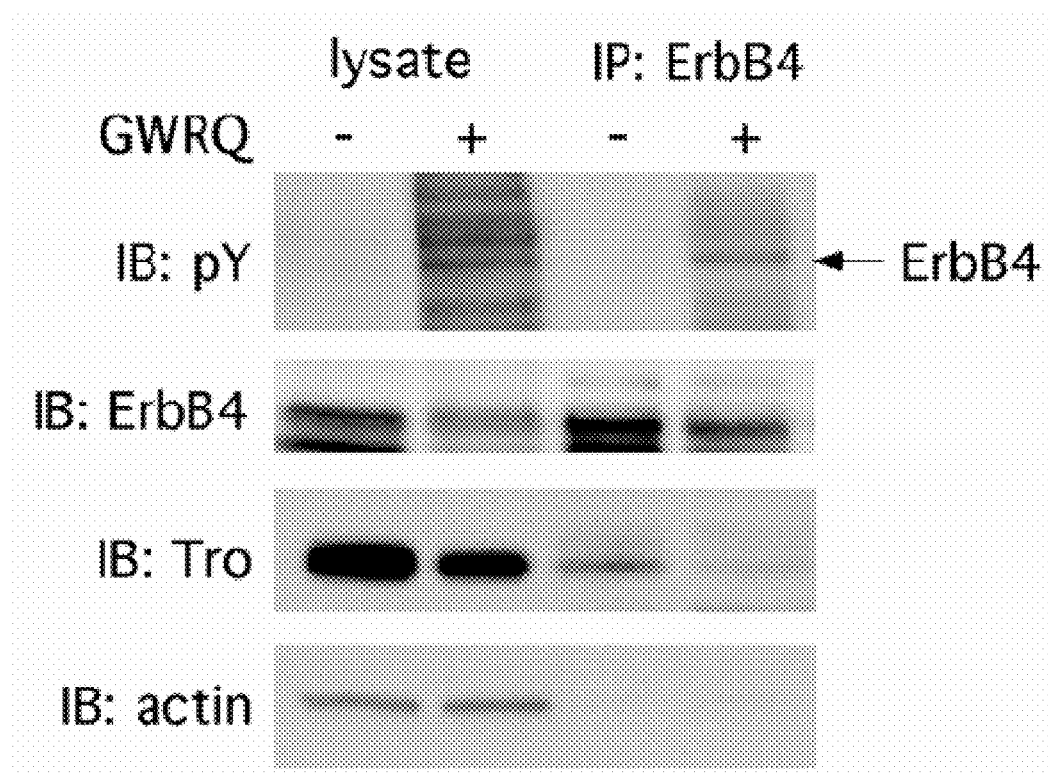
FIG. 3C shows tyrosine phosphorylation of ErbB4 in HT-H cells stimulated by GWRQ peptide. HT-H cells were treated with GWRQ peptide following stimulation for phosphorylation at 37° C. for 30 min.

EGF caused EGFR phosphorylation in A431 cells cultured in serum-depleted medium (FIG. 2B, lane 3). Strikingly, EGF caused no detectable EGFR phosphorylation in HT-H cells under the same conditions (FIG. 2B, lane 7). While the GWRQ had no effect on tyrosine phosphorylation in A431 cells (FIG. 2B, lane 4), in HT-H cells tyrosine phosphorylation occurred only when both EGF and GWRQ were added (FIG. 2B, lane 8). These results indicate that trophinin occupancy is critical for EGFR phosphorylation in HT-H cells.

Figure 6:
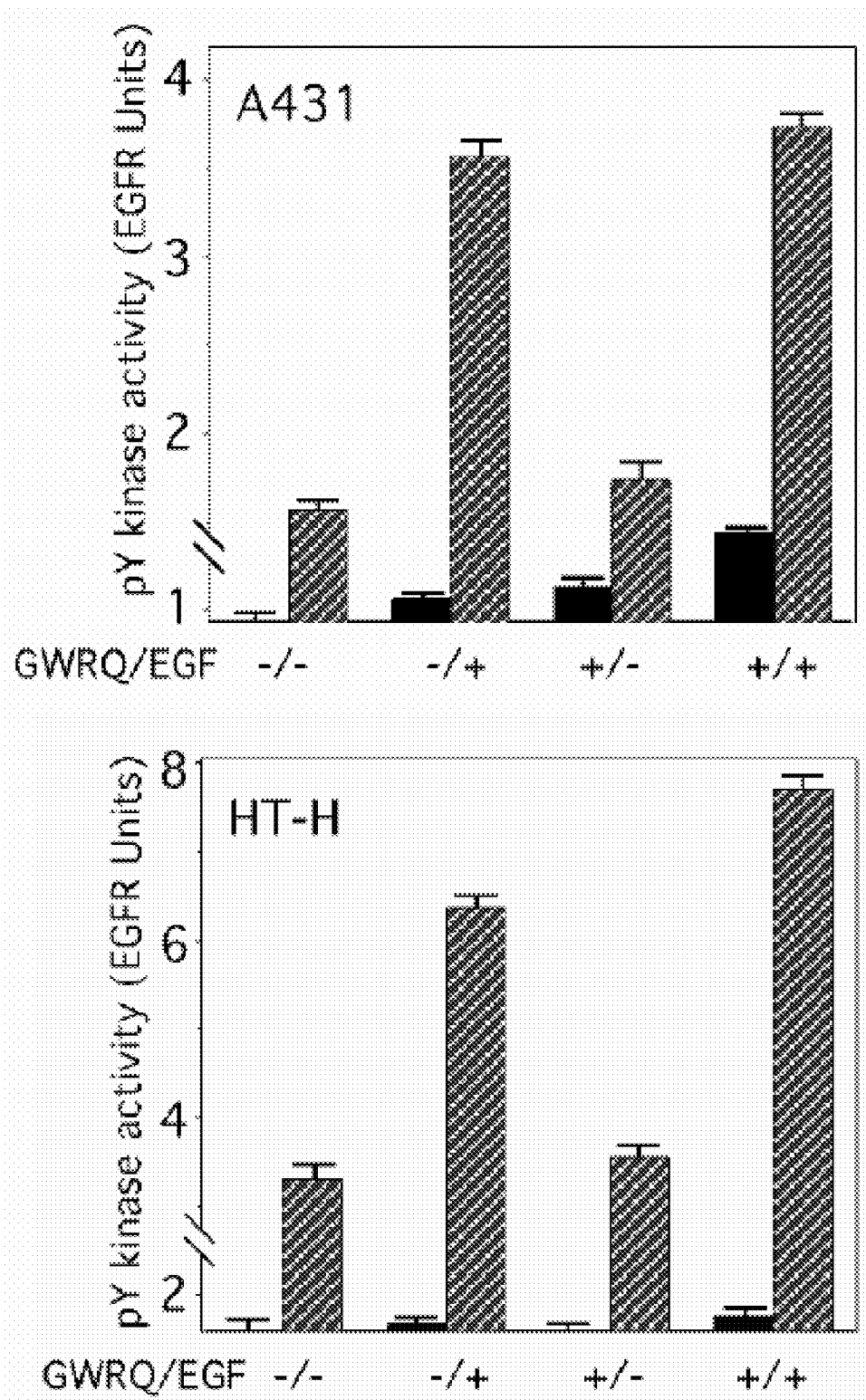
FIG. 6 shows tyrosine kinase activities of EGF- and/or GWRQ-treated A431 and HT-H cells. Each bar represents tyrosine kinase activity in immunoprecipitates with control IgG (black bar) and anti-ErbB4 antibody (hatched bar), with standard deviation.

Although HT-H cells express all four members of EGFR family (FIG. 3A) (Tada, J, et al. 1999), ErbB4 was the focus because trophectoderm cells of blastocysts express ErbB4 on apical cell membranes (Paria, B C, et al. 1999; Chobotova, K. et al. 2002). Tyrosine kinase activity assays revealed that EGF activated ErbB4 kinase activity both in A431 and HT-H cells (FIG. 6). GWRQ had no effect on ErbB4 kinase activity in A431 cells, while GWRQ somewhat increased this activity in HT-H cells. Given the complete absence of tyrosine phosphorylated proteins in the absence of GWRQ in HT-H cells (FIG. 2B, lane 7), these results indicate that trophinin blocks the susceptibility of EGFR as a substrate for tyrosine kinase, rather than inhibiting its enzymatic activity.

Figure 7A:
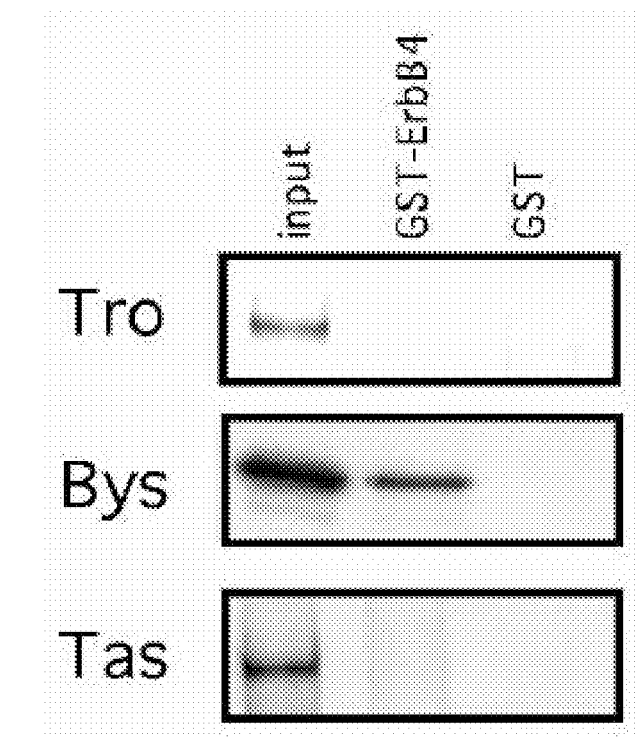
FIG. 7A shows pull-down assay for trophinin, bystin, and tastin, by GST-ErbB4. In vitro translated [$^{35}$S]-labeled trophinin, bystin or tastin was incubated with GST or GST-ErbB4 immobilized on glutathione beads. Bead-bound materials were visualized by autoradiography after gel electrophoresis.
Figure 7B:
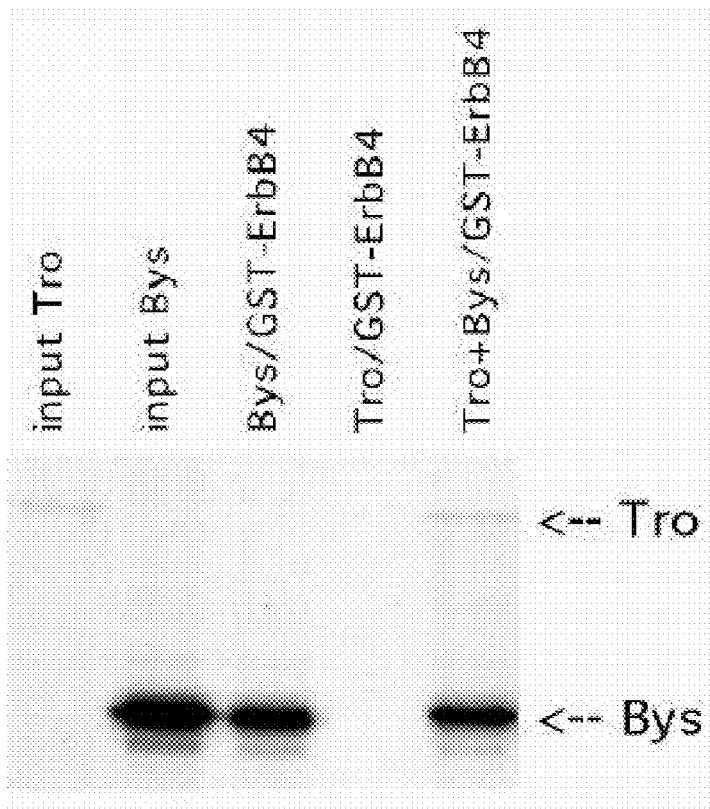
FIG. 7B shows pull-down assay of trophinin and bystin by GST-ErbB4. Bead-bound materials were visualized by autoradiography. Note that trophinin is captured by GSTErbB4 when bystin is present.

The cytoplasmic domain of trophinin directly interacts with bystin (Suzuki, N, et al. 1998), and bystin interacts with the proline-rich protein tastin (Nadano, D, et al. 2002). As the cytoplasmic domain of ErbB4 is proline rich (Komuro, A, et al. 2003), it was evaluated if trophinin and/or bystin interacts with the cytoplasmic domain of ErbB4. In vitro pull down assays revealed that bystin, but not trophinin or tastin, binds to the cytoplasmic domain of ErbB4 (FIG. 7A). When a mixture of trophinin and bystin was incubated with GST-ErbB4, trophinin bound to ErbB4, presumably through bystin (FIG. 7B).

Figure 7C:
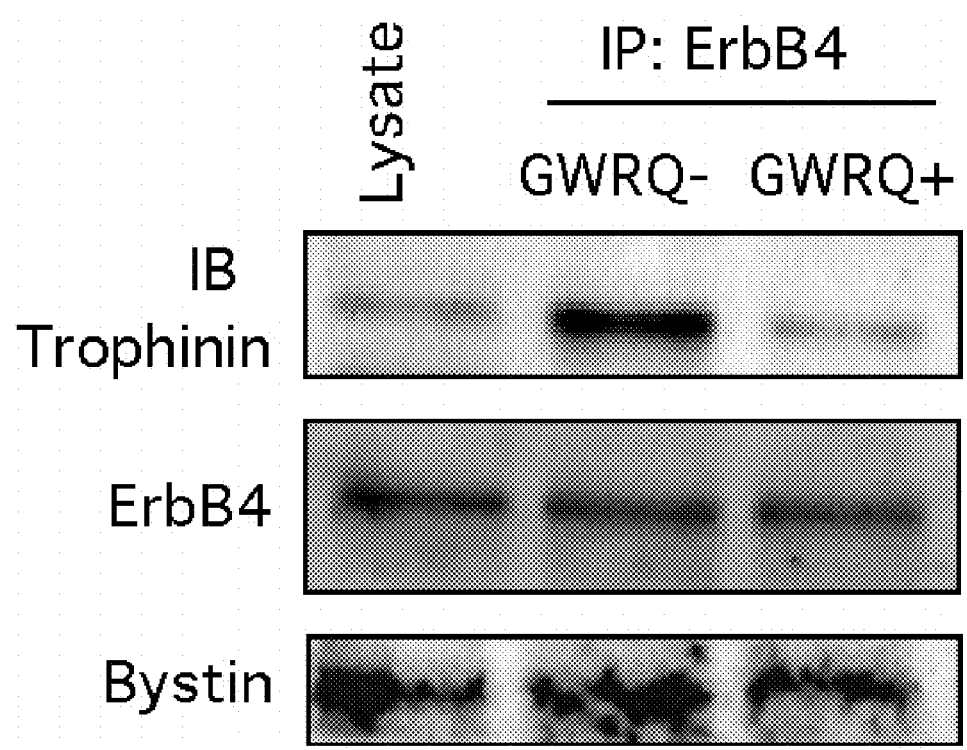
FIG. 7C shows interaction of trophinin, bystin and ErbB4 in HT-H cells. HT-H cells treated with or without GWRQ peptide were subjected to immunoprecipitation with antiErbB4 antibody, followed by western blot analysis. Note that trophinin and bystin were co-immunoprecipitated with ErbB4 from cells not treated with GWRQ, whereas less trophinin was present in precipitates from GWRQ-treated cells.

To determine if trophinin, bystin and ErbB4 interact with each other in HT-H cells, HT-H cell lysates were subjected to immunoprecipitation. Both trophinin and bystin co-immunoprecipitated with ErbB4 in the absence of GWRQ (FIG. 7C, top and bottom rows). Strikingly, trophinin levels were reduced in immunoprecipitates when HT-H cells were bound with GWRQ (FIG. 7C, top row, right). By contrast, bystin levels in the immunoprecipitates were not affected by GWRQ (FIG. 7C, bottom row).

Figure 8:
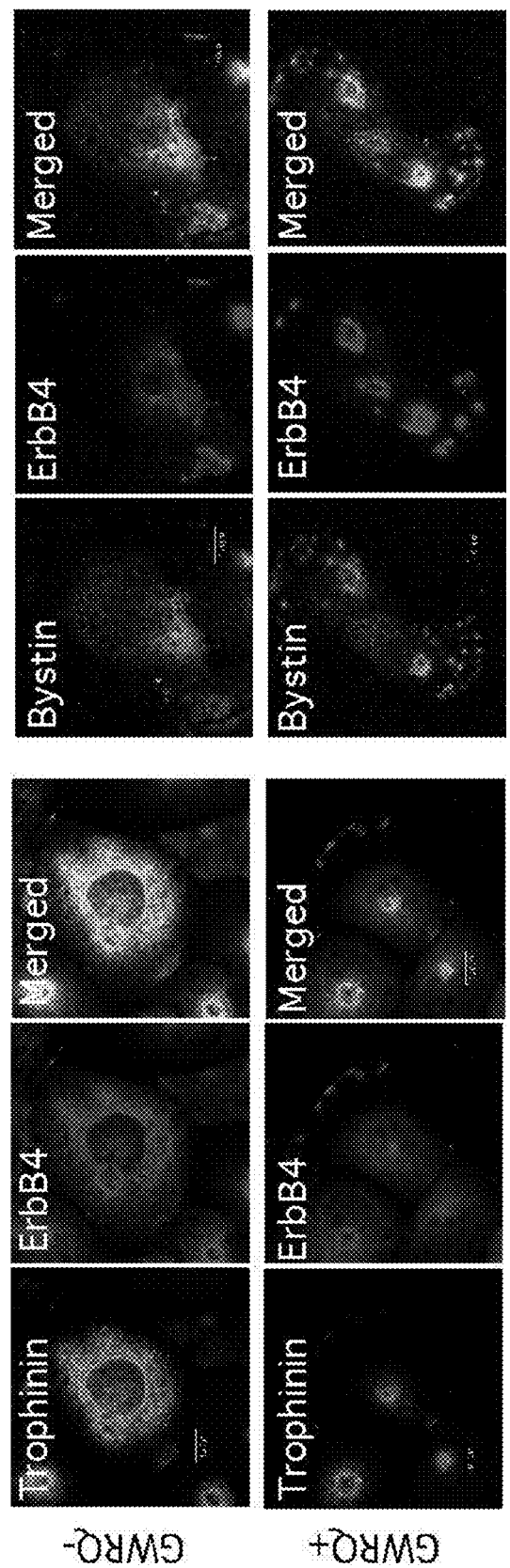
FIG. 8 shows confocal immunofluorescence micrographs of HT-H cells cultured with or without GWRQ peptide. Left: localization of trophinin and ErbB4. Right: localization of bystin and ErbB4.

Immunofluorescence microscopy of HT-H cells doubly stained for trophinin and ErbB4 on the cell surface showed overlap of these two proteins in the absence of GWRQ (FIG. 8, upper left). In HT-H cells treated with GWRQ, trophinin localized to the area above nuclei, and ErbB4 moved to the cell periphery (lower left). Bystin and ErbB4 co-localized in the absence of GWRQ (FIG. 8, upper right), but in GWRQ-treated HT-H cells, bystin had shifted to the cell periphery together with ErbB4 (FIG. 8, lower right). These results indicate that, in the absence of GWRQ, trophinin, bystin and ErbB4 form a complex, whereas in GWRQ-treated HT-H cells, ErbB4-bystin complex dissociates from trophinin. Therefore, in the absence of trophinin occupance at the cell surface, the cytoplasmic domain of ErbB4 is arrested by trophinin through bystin. Upon GWRQ binding, and potentially also when trophinin-mediated cell adhesion occurs, ErbB4 is released from this arrest and receptor autophosphorylation can take place.

Figure 9:
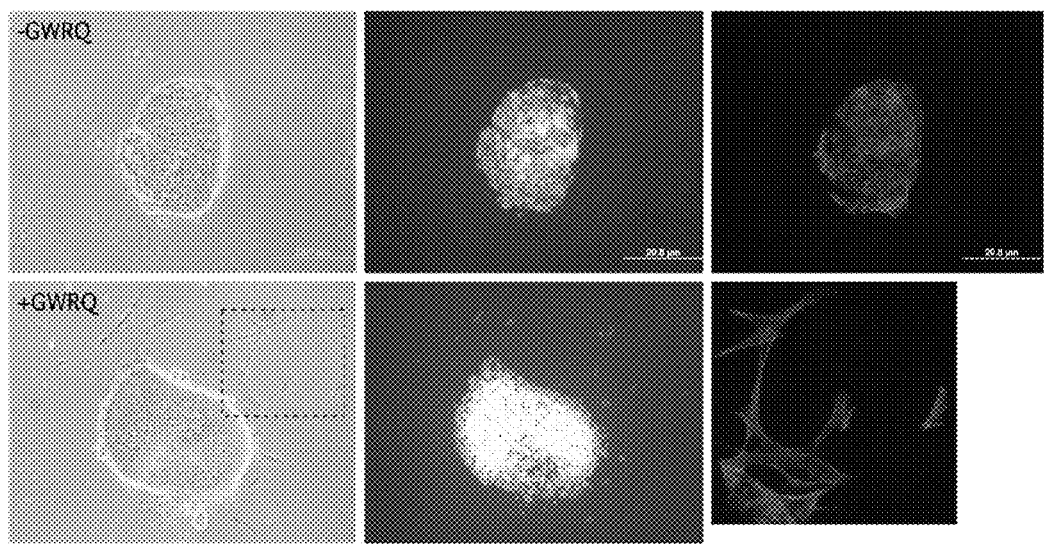
FIG. 9 shows effect of GWRQ peptide on monkey blastocysts. Rhesus monkey blastocysts were cultured in vitro in the absence (upper panel) or presence (lower panel) of GWRQ peptide. Phase contrast (left), DAPI stained (center), and Phalloidin staining of actin stress fibers (right) are shown.

To evaluate the in vivo relevance of these findings, the effect of the GWRQ peptide was tested on monkey blastocysts (FIG. 9). When fertilized monkey eggs were cultured in vitro to the blastocyst stage (Threadgill, D W, et al. 1995), trophectoderm cells loosely adhered to a fibronectin-coated cover glass, and there was no cell spreading (FIG. 9, upper panel). In cultures containing GWRQ peptide, trophectoderm cells not only adhered firmly, but also spread out from the cell mass (FIG. 9, lower panel). The spread cells were strongly stained for actin stress fibers.

EGFR has been implicated in mouse embryo implantation (Paria, B C, et al. 1999; Das, S K, et al. 1994; Paria, B C, et al. 2002), where an interaction between ErbB4 expressed on the trophectoderm and membrane-bound heparin binding EGF expressed on the uterine epithelium mediates an initial adhesion in mouse embryo implantation (Das, S K, et al. 1994). By placing ErbB4 downstream of trophinin in humans, disclosed herein is a link in the underlying mechanisms of human and mouse embryo implantation.

As cell adhesion is closely related to proliferation and differentiation, there is intense interest in signal transduction pathways initiated by cell adhesion (Giancotti, F G, et al. 1999; Cavallaro, U, et al. 2004). The trophinin-controlled signaling mechanism described herein is important in implantation and serves as a model for other cellular activation events in embryogenesis.

As disclosed herein, a single linear GWRQ peptide (monomeric GWRQ peptide) had the same effect as an octameric branched GWRQ peptide (GWRQ-MAP), but at about 100 times less efficiency. For example, 200-500 µg/ml monomeric GWRQ peptide was needed to activate HT-H cells, whereas 2-5 µg/ml of GWRQ-MAP was sufficient.

ii. Materials and Methods.

a. Antibodies and Reagents

The monoclonal anti-trophinin antibody (clone 3-11, mouse IgM) and anti-bystin antibody (clone 19, mouse IgM) were generated as described previously (Suzuki, N, et al. 1999). A monoclonal anti-tyrosine phosphate antibody (clone 4G10, mouse IgG) was obtained from Upstate Biotechnology. Polyclonal rabbit anti-epidermal growth factor receptor (EGFR) was obtained from Santa Cruz Biotechnology. Monoclonal anti-ErbB2 antibodies (mouse IgG, OP15) were obtained from Calbiochem. Rabbit anti-ErbB2 antibody and rabbit anti-ErbB3 antibody were obtained from Stratagene. A rabbit anti-ErbB4 antibody directed at the cytoplasmic domain was obtained from Santa Cruz Biotechnology, and a rabbit antibody directed to the ErbB4 ectodomain was obtained from Abgent. Monoclonal anti-alkaline phosphatase antibody (clone H7, mouse IgG2a) (Millan, J.-L, et al. 1983) was obtained. Rhodamine-phalloidan was obtained from Molecular Probes. GWRQ-MAP, in which eight GWRQ peptides linked to a branched lysine cluster (MAP), were synthesized by AnaSpec, San Jose, Calif. Control peptides (branched alanine peptides) and irrelevant branched peptides (Fukuda, M N, et al. 2000) were also synthesized by AnaSpec.

b. Antibody Cross-Linking and Stimulation of Phosphorylation

HT-H cells were cultured as a monolayer in a tissue culture plate or on a glass coverslip. Cells were incubated on ice for 15 min with phosphorylation medium, which is composed of high glucose DME supplemented with 25 mmole/L Hepes, pH7.2, 0.1% bovine serum albumin, and 0.2 mmole/L $Na_3VO_4$. Cells were then incubated with or without antitrophinin antibody (2 µg/ml) for 30 min, followed by goat anti-mouse IgM antibody (25 μg/ml) at 4° C. Cells were then warmed to 37° C. and cultured for 0~60 min to stimulate phosphorylation. Cells were then subjected to immunocytochemistry, immunoprecipitation and/or Western blot analysis (see below).

c. Phage Library Screening

An M13 phage library (~$10^{11}$ clones) for random 10-mer peptides was constructed as described (Koivunen, E, et al. 1994). Target HT-H cell monolayers were grown in one 24 well plate and fixed with 1% paraformaldehyde in PBS. After washing with PBS containing 1 mM EDTA, the monolayer was blocked with PBS containing 5% BSA, and the phage solution (containing 1013 colony forming units) was added to HT-H cells. After incubating at room temperature for 15 min, unbound phage was washed with 1 mM EDTA/PBS, and HT-H bound phage was recovered by transforming K91 *E. coli* bacteria. Selected phage was amplified in LB medium containing tetracycline (20 μg/ml) and kanamycin (100 μg/ml) and subjected to a second round of screening using HT-H cells as a target. After a third enrichment, individual clones were sequenced.

d. Phage Binding Assay by Colony Counting

HT-H cells and control A431 cells were grown in 96 well plates to confluency. Cells were fixed with 1% paraformaldehyde in PBS and blocked with 5% BSA in PBS. A phage solution containing 1×105 pfu suspended in 10 μl mM EDTA in PBS, was added to each well and incubated at room temperature for 15 min. After washing unbound phage with PBS, freshly prepared K91 competent cells were added to each well. After incubation for 60 min, K91 cells were plated on an LB agar plate containing kanamycin (100 μg/ml) and tetracycline (20 μg/ml). After culturing at 37° C. for 20 hours, the number of colonies on the plate was counted.

e. Inhibition of Phage Binding by Anti-Trophinin Antibody

To determine the effect of anti-trophinin antibody on phage binding, HT-H cells grown in 96 well plates were fixed and blocked as described above. HT-H cells were incubated at room temperature for 30 min with 1 mM EDTA and 5% BSA in PBS, containing antitrophinin antibody (5 μg/ml), anti-alkaline phosphatase antibody (5 μg/ml) or no antibody. A solution of 1×$10^5$ pfu in 10 μl was then added and incubated for 15 min. After washing with PBS, phage bound to HT-H cells were scored as described above.

f. Inhibition of GWRQ Peptide Binding to HT-H Cells by an Anti-Trophinin Antibody HT-H cells were grown in flat-bottomed 96 well plates to confluency and fixed with 1% paraform aldehyde in PBS. Fixed HT-H cells were treated with 0.3% hydrogen peroxide in PBS for 30 min to inactivate endogenous peroxidase. After blocking with 5% BSA in PBS, cells were incubated with anti-trophinin antibody or irrelevant anti-alkaline phosphatase antibody as described above. Biotinylated GWRQ-MAP peptide (10 μl, 40 ng) was then added to the wells and incubated for 15 min. After washing with PBS, biotinylated peptide bound to HT-H cells was reacted with 1:1000 diluted peroxidase-conjugated streptavidin (Pierce) for 15 min. After washing with PBS, wells were reacted with peroxidase substrate ABTS (Pierce) to evaluate a color reaction, and absorbance at 405 mm was measured by a microplate reader (Molecular Devices).

g. Immunoprecipitation by Anti-Phage Antibody and Western Blot Analysis

HT-H cells were grown to confluency in 10 cm tissue culture plates. GWRQ peptide displaying phage (1×$10^8$ cfu) was added to the monolayer and incubated at 4° C. for 15 min. Controls were undertaken by incubating HT-H cells with phage without insert. After washing with cold PBS, HT-H cells were scraped using rubber policemen, collected by centrifugation, and solubilized in 1% deoxycholate in PBS. Cell lysates were incubated with rabbit anti-M13 (fdtet) antibody (Sigma), and immune complexes were collected by protein A agarose beads (Sigma). Controls were cell lysates treated with rabbit IgG. Immunoprecipitates were eluted from beads by boiling in SDS sample buffer. Proteins were resolved in SDS-PAGE and transferred to PVDF membranes. PVDF membranes were blocked with PBS containing 5% BSA and then incubated with anti-trophinin antibody at room temperature for 60 min. After washing with PBS containing 0.02% Tween 20, membranes were reacted with diluted peroxidase conjugated goat anti-mouse Ig antibody (Cappel) for 60 min. Immunoreactive bands were visualized by chemiluminescent peroxidase substrate ECL and exposure to X-ray film. Western blot analysis for other antigens, i.e., bystin, ErbB4, and tyrosine phosphate, was carried out in a similar manner as trophinin.

h. Western Blot for Phosphorylated Proteins

Tyrosine phosphorylated proteins were detected by anti-phosphotyrosine antibody (4G10, mouse IgG). HT-H cells and A431 cells were grown in 10 cm plates to semi confluency, incubated in phosphorylation medium with GWRQ peptide (GWRQ-MAP; 2 μg/ml) at 4° C. for 15 min, and stimulated for phosphorylation at 37° C. for 0 min 120 min. Control HT-H cells were treated in the same manner without GWRQ peptide. HT-H cells were harvested using rubber policemen, collected by centrifugation, and washed once with cold PBS. Cells were lysed with 0.5% NP-40 in PBS containing phosphatase inhibitors (30 mM NaF, 40 mM β-glycerophosphate, 20 mM Na pyrophosphate, and 1 mM $Na_2VO_4$) and protease inhibitors (2 mM EGTA, 5 mM EDTA, 1 mM phenylmethylsulfonylfluoride, 3 mM benzamidine, 5 μM pepstatin A, 10 μM leupeptin). Western blot was carried out as described above.

Screening of phosphorylated proteins by phospho specific antibodies was carried out by Kinexus, Vancouver, B. C., Canada. HT-H cells and A431 cells grown as monolayers were serum starved by culturing in medium lacking FCS for 2 days. Cells were incubated in phosphorylation medium without FCS and then stimulated at 37° C. for 0 min~120 min in medium containing recombinant human EGF (20 ng/ml) with or without GWRQ peptide.

i. RT-PCR for ErbB Transcripts

Total RNA was prepared from HT-H cells using TRIzol reagent (Gibco BRL). RT reaction was performed using Superscript reverse transcriptase and oligo dT primer (Invitrogen). Following primers were used for PCR.

```
ErbB1 forward,
5'-ACAGGTGCGAATGACAGTAGCAT-3';      (SEQ ID NO: 5)

ErbB1 reverse,
5'-ACCATTTCTTCCTTGATAAATTGGATG-3';  (SEQ ID NO: 6)

ErbB2 forward,
5'-CAAATTAGGAACCTTGCAACGGT-3';      (SEQ ID NO: 7)

ErbB2 reverse,
5'-TCCCCTGGGTCTTTATTTCGTC-3';       (SEQ ID NO: 8)

ErbB3 forward,
5'-TTGATAACCCTGATTACTGGCATAGC-3';   (SEQ ID NO: 9)

ErbB3 reverse,
5'-TGAGAGGAAGGGATATGGAGAGTAATC-3';  (SEQ ID NO: 10)
```

```
ErbB4 forward,
5'-GAATAGGAACCAGTTTGTATACCGAG-3';     (SEQ ID NO: 11)

ErbB4 reverse,
5'-CTTGTTTGGGTTTGTCTCGCAT-3'.         (SEQ ID NO: 12)
```

PCR reaction was: after denaturing at 96° C. for 5 min, 35 cycles of denaturing at 96° C. for 30 sec, annealing at 55° C. for 30 sec, and extension at 72° C. for 1 min, which followed an extension at 72° C. for 7 min.

j. Immunofluorescence and Confocal Fluorescence Microscopies

HT-H cells grown on a glass coverslip were fixed with 1% paraformaldehyde in PBS at room temperature for 15 min (Yamaguchi, N, et al. 1995). For staining with rhodamine-phalloidan, cells were fixed with cold methanol for 15 min. For immunostaining with anti-ErbB4 antibody (Abgent), cells were fixed with buffered-formalin (1:1 mixture of PBS and 37% formaldehyde) at room temperature for 15 min. After washing with PBS, fixed cells were incubated with PBS containing 10% goat serum for 30 min with or without 0.1% saponin and incubated with the first antibody for 60 min., followed by incubation with a fluorescence-conjugated second antibody for 60 min. A Zeiss fluorescence microscope (Axioplan model 5) equipped with an Olympus DP-70 camera was used. Confocal and Nomarski differential-interference-contrast images were obtained using a Fluoroview laser-scanning microscope (Olympus). Z-sections were recorded at 0.5~1 μm intervals and all sections were merged.

k. Wound Healing Assay

HT-H cells were grown on a glass coverslip to near confluency. The HT-H monolayer was scratched by a plastic pipet tip to create a wound, and cultured up to 7 hours in DME medium containing 10% fetal calf serum with or without GWRQ peptide (2 μg/ml). The HT-H monolayer at the wounded region was monitored for recovery and photographed under an inverted microscope.

l. Transwell Assay of Motility and Invasion

Cellular motility and invasion were evaluated using a transwell apparatus (6 well plate, pore size 8 nm, Becton-Dickinson) with an insert of uncoated polycarbonate filter and Matrigel-coated filter, respectively. HT-H cells ($1 \times 10^5$) were plated in the upper chamber and incubated at 37° C. for 20 hours in medium containing 10% fetal calf serum with or without GWRQ peptide (2 μg/ml). Cells that did not migrate through the membrane were removed by scrubbing, and cells that migrated to the lower face of the membrane were fixed with methanol and stained with crystal violet. The number of cells on the lower face was counted under the microscope. The mean number of 10 randomly selected fields was plotted.

m. Cell Proliferation Assays

Proliferation of HT-H cells was determined using a BrdU (5'-bromo-2'-deoxy-uridine) incorporation assay (Gratzner, H. G. 1982) with a BrdU labeling and detection kit (Roche Molecular Biochemicals). Briefly, HT-H cells were grown to 50% confluency. After adding BrdU, cells were cultured at 37° C. for 60 min. Cells were fixed with ethanol, washed with PBS, and incubated with anti-BrdU antibody at 37° C. for 30 min. After further washing with PBS, cells were incubated with fluorescein-conjugated anti-mouse Ig at 37° C. for 30 min. After washing with PBS, cells were mounted with Vectashield with DAPI (Vector). The ratio of immunostained cells to DAPI stained cells represents proliferation activity of the cells. The mean number of 3 randomly selected fields was obtained.

n. EGF Binding Assay

HT-H cells, A431 cells, and MRC-5 cells were grown in a 24 well plate in high glucose DME containing 10% fetal calf serum, 1 mM pyruvate, 5 mM glutamate, penicillin (100 units/ml) and streptomycin (100 units/ml) to subconfluency. Cells were washed with culture medium without fetal calf serum and cultured in medium without fetal calf serum for two days. Before determining EGF binding, the culture medium was replaced with fresh medium without serum, placed on ice, and recombinant EGF 25 ng in 100 μl PBS was added to each well. After incubation at 4° C. for 30 min, cells were washed with cold PBS three times, and solubilized with 1% NP-40 in PBS. Cell lysates were centrifuged, and the clear supernatant was subjected to a sandwich ELISA provided by the EGF assay kit (Biosource). Levels of EGF in lysates were quantitated using the EGF standard included in the kit.

o. Tyrosine Kinase Activity Assay

A431 cells and HT-H cells were cultured in 10 cm plate to sub-confluency.

Medium was replaced with DME without FCS, and cells were cultured for 3 days without FCS by exchanging medium every day. To HT-H or A431 monolayer kept at 4° C., $Na_3VO_4$ was added to 1 mM. GWRQ peptide (5 μg/ml) and/or recombinant human EGF (20 ng/ml) was added to each plate, and left at 4° C. for 30 min. Cells were harvested by rubber policeman, and washed with cold PBS. Cells were lysed in PBS containing 1% NP-40, and cell lysate was subjected to immunoprecipitation with 20 & I protein A beads pre-coated with control IgG or with rabbit anti-ErbB4 antibody (Sant Cruz Biotechnology). Immunoprecipitates were washed with cold PBS and suspended in cold PBS. A polyvinylchloride ELISA plate (Falcon) was coated with tyrosine kinase substrate poly EY (Sigma) in PBS (1 μg/100 μl) at 4° C. for 20 hours. After washing the plate, each immunoprecipitate as triplicate was added to each well in 100 & I kinase assay buffer (50 mM Hepes buffer, pH 7.4, 20 mM $MgCl_2$, 1 mM $MnCl_2$, 2 mM $Na_3VO_4$, and 0.4 mM ATP), and reacted at room temperature for 30 min. Plate was washed with TBS, and reacted with diluted (1:5000) anti-tyrosine phosphate antibody (4G10) for 1 hour, and reacted with peroxidase-conjugated goat anti-mouse IgG antibody. After washing wells with TBS, peroxidase substrate ABTS (Pierce) was added and developed color was read in an ELISA reader at 405 mm.

p. GST-ErbB4 Pull-Down Assay

The cytoplasmic domain of human ErbB4 was expressed in bacteria as a GST-fusion protein as follows. cDNAs were prepared from human kidney RNA (Clontech) and sequences encoding the ErbB4 cytoplasmic domain were amplified by PCR. Primers used were:

```
                                         (SEQ ID NO: 13)
    F1,    5'-ACCCGGGAAAGAGCATCAAAAAGAAAAG-3';

(SEQ ID NO: 14)
    R1,    5'-GGCAGCCATGGGGCATAA-3';

(SEQ ID NO: 15)
    F2,    5'-CAACTTATGCCCCATGGCT-3';

(SEQ ID NO: 16)
    R2,    5'-ATCATATCTTCCAAATCCTCTTCATC-3';

(SEQ ID NO: 17)
    F3,    5'-ATCGTATGAAGCTTCCCAGTCC-3';

(SEQ ID NO: 18)
    R3,    5'-AACTGAGCTTACACCACAGTATTCC-3'.
```

Each product was subcloned into the TA vector of BluescriptII KS+, and the insert was sequenced. Each verified F1~R1 and F2~R2 was released from pBluescript as an XmaI~NcoI fragment and an NcoI~HindIII fragment, respectively, and ligated into the XmaI and HindIII sites of pGEX-KG to produce F1~R2/pGEX-KG. Sequence-verified F3~R3 in pBluescript was digested with HindIII and ligated into the HindIII site of F1~R2/pGEX-KG to produce F1~R3/pGEXKG. Competent DH5 alpha bacteria was transformed and clones verified by restriction digestion. Bacteria transformed by pGEX-KG-ErbB4 were amplified in LB containing ampicillin, GST-ErbB4 fusion protein was induced by IPTG, and the fusion protein was purified by glutathione Sepharose beads (Pharmacia).

A GST-fusion protein pull-down assay was carried out as described (Swaffield, J C, et al. 1996). Trophinin, bystin, and tastin proteins were produced as [$^{35}$S]-methionine labeled proteins using an vitro transcription and translation kit (TnT, Promega), according to the manufacturer's protocol. [$^{35}$S]-trophinin, [$^{35}$S]-bystin, and [$^{35}$S]-tastin were mixed individually with GSTErbB4 immobilized on glutathione beads in binding buffer (Swaffield, J C, et al. 1996) at 4° C. for 1 hour. After washing unbound materials with binding buffer, bead-bound material was eluted by boiling in SDS sample buffer. [$^{35}$S]-labeled proteins eluted were analyzed by SDS-PAGE followed by fluorography.

q. Animals

Mature rhesus macaque males and females housed in individual cages were used in this study.

r. Ovarian Stimulation, Recovery of Rhesus Macaque Oocytes, Fertilization by ICSI, Embryo Culture and Trophinin Treatment Controlled ovarian stimulation and oocyte recovery has been described previously (Zelinski-Wooten, M B, 1995). Briefly, cycling females were subjected to follicular stimulation using twice-daily intramuscular injections of recombinant human FSH as well as concurrent treatment with Antide, a GnRH antagonist, for 8-9 days. Unless indicated, all reagents were from Sigma-Aldrich Co. (St. Louis, Mo.) and all hormones were from Ares Advanced Technologies Inc. (Norwell, Mass.). Females received recombinant human LH (source) on days 7-9 and recombinant hCG on day 10. Cumulus-oocyte complexes were collected from anesthetized animals by laparoscopic follicular aspiration (28-29 hrs post HCG) and placed in Hepes-buffered TALP (modified Tyrode solution with albumin, lactate and pyruvate) medium (Bavister, B D, et al. 1977) containing 0.3% BSA (TH3) at 37° C. Oocytes, stripped of cumulus cells by mechanical pipetting after brief exposure (<1 min) to hyaluronidase (0.5 mg/ml), were placed in chemically defined, protein-free HECM-9 medium (Hamster Embryo Culture Medium) McKiernan, S H, et al. 2000) at 37° C. in 5% $CO_2$, 5% $O_2$ and 90% $N_2$ until further use.

Fertilization by intracytoplasmic sperm injection (ICSI) and embryo culture were performed as described (Wolf, D P, et al. 2004). Briefly, sperm were diluted with 10% polyvinylpyrrolidone (1:4; Irvine Scientific, Santa Ana, Calif.) and a 5 µl drop was placed in a micromanipulation chamber. A 30 µl drop of TH3 was placed in the same micromanipulation chamber next to the sperm droplet and both were covered with paraffin oil (Zander IVF, Vero Beach, Fla.). The micromanipulation chamber was mounted on an inverted microscope equipped with Hoffman optics and micromanipulators. An individual sperm was aspirated into an ICSI pipette (Humagen, Charlottesville, Va.) and injected into the cytoplasm of a metaphase II arrested (MII) oocyte, away from the polar body. After ICSI, injected oocytes were placed in 4-well dishes (Nalge Nunc International Co., Naperville, Ill.) containing protein-free HECM-9 medium and cultured at 37° C. in 6% $CO_2$, 5% $O_2$ and 89% $N_2$. Cultures were maintained under paraffin oil. Embryos at the 8-cell stage were transferred to fresh plates of HECM-9 medium supplemented with 5% fetal bovine serum (FBS; HyClone, Logan, Utah) and cultured until hatching with a medium change every other day. After hatching blastocysts were placed into cell-culture treated chamber slides (Nunc) and allowed to adhere. After adhesion, half of the embryos were treated with trophinin (5 g/ml) for two days and the rest were cultured as negative controls in HECM9+10% FBS. After treatment the embryos were fixed and DAPI stained, and cell outgrowths were analyzed.

2. Example 2

The Trophinin-Binding Peptide GWRQ Promotes Human Sperm Motility i. Introduction Trophinin mediates apical cell adhesion between trophectoderm and endometrial epithelia, through trophinin-trophinin binding, which occurs in the initial stages of human embryo implantation (Fukuda, M. N., et al. 1995; Suzuki, N., et al. 1999; Nakayama, J., et al. 2003; Nadano, D., et al. 2002). In human trophoblastic cells, the trophinin intracellular domain is bound by the cytoplasmic protein bystin (Suzuki, N., et al. 1998). Formation of this complex arrests the activity of ErbB4, an ErbB family receptor tyrosine kinase (Sugihara, K., et al. 2007; Fukuda, M. N., et al. 2007). When trophinin-mediated cell adhesion occurs, bystin dissociates from trophinin, releasing ErbB4 from arrest and allowing it to autophosphorylate. a peptide-displaying phage library was screened using a trophinin-expressing human trophoblastic HT-H cell line as a target and identified a trophinin-binding peptide, GWRQ (Sugihara, K., et al. 2007). Multivalent 8-branched GWRQ peptide (GWRQ-MAPS) bound to the trophinin extracellular domain, mimicking trophinin-mediated cell adhesion and transducing signals promoting trophectoderm activation (Sugihara, K., et al. 2007; Fukuda, M. N., et al. 2007).

Trophinin is highly expressed in mouse testis, ovary and brain (Nadano, D., et al. 2002; Saburi, S., et al. 2001). To investigate its role in vivo trophinin-deficient knockout mice was generated (Nadano, D., et al. 2002). Trophinin nulls were born without significant defects, indicating that trophinin does not play an essential role in embryo implantation in the mouse (Nadano, D., et al. 2002), and, in fact, other studies support the idea that its role in embryo implantation is unique to humans (Nakayama, J., et al. 2003; Suzuki, N., et al. 2000; Aoki, R., et al. 2006). However, it was observed that spermatozoa from trophinin null male mice older than 5-months were significantly immotile. Given that trophinin protein is found in the tail of mouse sperm (Saburi, S., et al. 2001), these observations suggested a role of trophinin in sperm tail motility.

Two trophinin-associated cytoplasmic proteins, bystin and tastin were identified (Fukuda, M. N., et al. 1995; Suzuki, N., et al. 1998; Fukuda, M. N., et al. 1999; Miyoshi, M., et al. 2007). A yeast two-hybrid library screen for tastin-interacting proteins identified Tctex-1, a light chain of dynein or microtubule-associated ATPase, indicating that tastin binds to microtubules probably through dynein. Sperm flagella use ATP as an energy source (Summers, K. E., et al. 1971; Turner, R. M. 2003). ATPs are generated by mitochondria in the mid-pierce or lower portion of the sperm head and supplied to the tail, which consists of microtubules and microtubule-associated motor dynein. When dynein hydrolyzes ATP microtubules slide against one another, translating energy to flagella motility.

Disclosed is an analysis of the function of trophinin in human sperm motility using GWRQ-MAPS peptide as a tool. The results show that human sperm contains trophinin, bystin and tastin proteins in the tail and that sperm moves vigorously in medium containing GWRQ-MAPS, which reduced ATP levels and increased intracellular calcium in sperm cells.

ii. Materials and Methods a. Synthetic Peptides, Antibodies

GWRQ-MAPS in which eight GWRQ peptides are linked to a branched lysine cluster (MAPS), and control synthetic peptides were synthesized by GenScript (Scotch Plains, N.J.). Monoclonal antibodies for trophinin, bystin and tastin were generated as described (Suzuki, N., et al. 1999). Monoclonal anti-trophinin antibody was from Upstate (Lake Placid, N.Y.). Rabbit anti-fd antibody against M13 phage was from Sigma.

b. Motility Assay of Human Sperm Treated with GWRQ-MAPS

Human sperm ($2-20\times10^7$ cells) from 4 healthy men (age, 35.75±3.4) were suspended in phosphate buffer saline (PBS) and divided into 4 groups: 2 were incubated with GWRQ-MAPS (2 µg/ml) and 2 were incubated with control peptide. After incubation at room temperature for 30 min, 50 ul of sperm solution was suspended in 950 µl PBS or 950 µl of paraformaldehyde (PFA) in PBS. The numbers of immotile sperm in PBS were counted using a hemocytometer, and the numbers of total sperm were counted in PFA in PBS. Numbers of motile sperm were obtained by subtraction of immotile from total sperm. In other experiments, human sperm ($5.76\times10^7$±2.97 cells) from 23 healthy men (age 25.5±2.5) were washed and suspended in sperm washing medium (Irvine Scientific, Santa Ana, Calif.). After determining motility, GWRQ-MAPS was added (15 µg/ml) and motility was compared after incubation 33° C. for 30 min.

c. Immunohistochemistry of Human Sperm for Trophinin, Bystin and Tastin

Human sperm from healthy men were suspended in PBS and smeared on glass slides. Cells were fixed in 4% PFA in PBS, followed by treatment with methanol containing 0.3% hydrogen peroxide. For trophinin staining, sperm were fixed with 4% PFA in PBS and then treated with 0.1N HCl at 80° C. for 1 hour. Slides were incubated with mouse IgM monoclonal antibodies for either trophinin, bystin or tastin (Suzuki, N., et al. 1999), followed by incubation with biotinylated anti-mouse IgM antibody (Vector) and with peroxidase-conjugated avidin. A peroxidase color reaction was performed using 3-amino-9-ethyl carbazole (AEC single solution, Zymed). Counter-staining was performed using hematoxylin.

d. Binding of GWRQ-Peptide Displaying Phage to Human Sperm

Human sperm cells on slides were fixed in 4% PFA in PBS. After washing with PBS, slides were treated with 0.1N HCl at 80° C. for 1 hour and then blocked with 1% bovine serum albumin in PBS at room temperature for 30 min. K91 kan bacteria infected with cloned M13-based phage displaying GWRQLTARVP (SEQ ID NO:4) peptide (Sugihara, K., et al. 2007) and bacteria with control phage without the displayed peptide were cultured in LB medium containing kanamycin (100 µg/ml) and tetracycline (10 µg/ml) at 37° C. for 20 hours. After centrifugation, polyethylene glycol 8,000 and NaCl were added to supernatant to final concentration 6% and 1.6M, respectively. After incubating at 4° C. for 20 hours, phage was precipitated by centrifugation. Phage pellets were suspended in PBS and overlaid on sperm cells fixed on slides. After washing with PBS, slides were fixed again in 4% PFA in PBS, and phage protein bound to sperm was detected by immunostaining using a rabbit anti-phage (fd) antibody (Sigma).

e. Quantitative Analysis of ATP

ATP production was assessed using a CellTiter-Glo Luminescent Cell Viability Assay Kit (Promega, Madison, Wis.). Human sperm from healthy men were washed twice using sperm washing medium (Irvine Scientific) and re-suspended in Hank's balanced salt solution with 20 mM HEPES buffer, pH 7.4, at $4.0\times10^5$ cells/ml. 50 µl of sample containing $2.0\times10^4$ sperm cells was placed in each well of a 96-well plate. After adding PBS and either GWRQ-MAPS or control peptides at 15 µg/ml to each well, 50 µl of CellTiter-Glo reagent was added to each well at time 0. Luminescence was recorded using a Veritas™ Microplate Luminometer (Turner Biosystems, Sunnyvale, Calif.) after incubation at room temperature for 10, 30 and 60 min.

f. Intracellular $Ca^{2+}$ Concentration in Human Sperm

Measurement of intracellular $Ca^{2+}$ was assessed using a Fluo-4 NW Calcium Assay kit (Molecular Probes, Eugene, Oreg.). Human sperm from healthy men were washed twice in sperm washing medium (Irvine Scientific) and re-suspended in buffer at $1.0\times10^6$ cells/ml. Sperm ($5.0\times10^5$ cells in 50 µl/well) were plated in a 96-well plate, and 2× dye loading solution (50 µl) was added to each well and incubated at 37° C. for 30 min. PBS and peptides (GWRQ-MAPS and control peptides at 15 µg/ml each) were added just before measurement, and $Ca^{2+}$ concentration was measured for 1 hour at room temperature. For luminometric analysis, an f-max Fluorescence Microplate Reader and SOFT max Pro ver. 1.1 (Molecular Devices, Sunnyvale, Calif.) were used, which analyzed kinetics by measuring fluorescence of each well every 20 seconds for 60 min. Quintuplet analysis was carried out for each sample.

g. Transwell Motility Assay of Human Sperm

Human sperm from 3 healthy men (age, 34.75±4.6) were washed twice in sperm washing medium and re-suspended in medium at $2.2-4.8\times10^7$ cells/ml. Transwell motility assay described by Narisawa et al., (Narisawa, S., et al. 2002) was used. A transwell culture chamber (Becton Dickinson, San Jose, Calif.) was used, and the bottom of the upper chamber was sealed with polyethylene terephthalate with 8 µm pores. Lower and upper chambers were filled with sperm washing medium containing PBS or PBS containing either GWRQ-MAPS or control peptides at 15 µg/ml. Sperm ($2.2-2.8\times10^5$ cells/100 µl) were added to the upper chamber and incubated at 37° C. for 2 hours. Cells migrating to the lower chamber were counted by hemocytometer. Triplicate measurements were performed for each sample.

iii. Results a. GWRQ Peptide Promotes Motility of Human Sperm

Figure 10A:
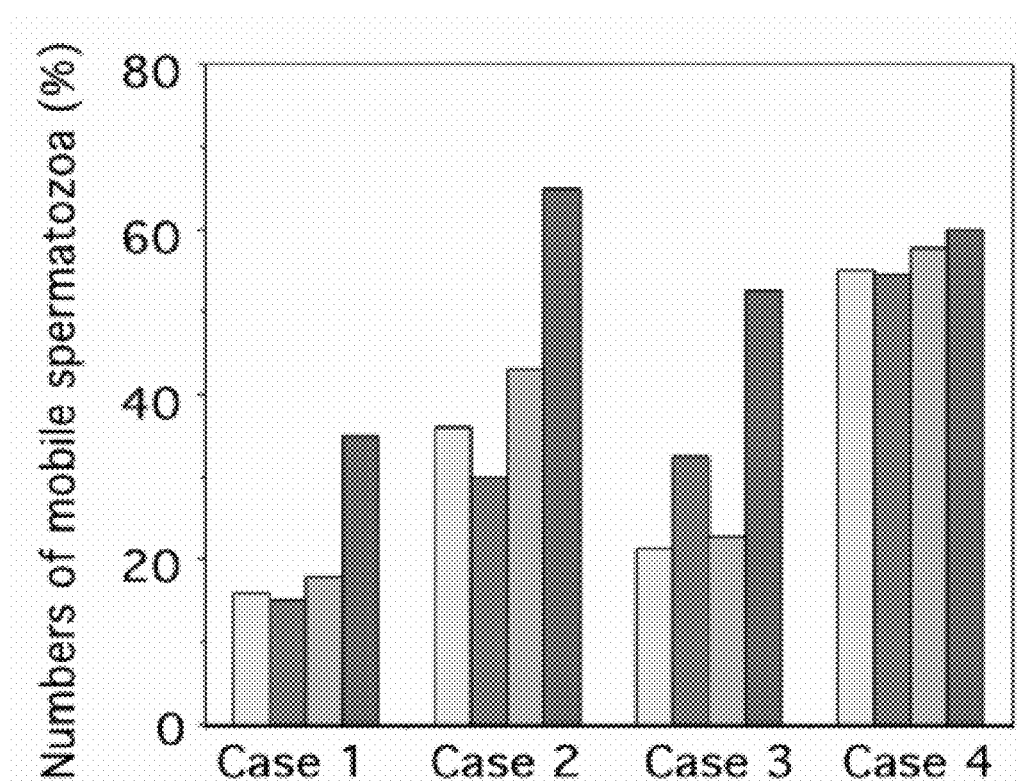
FIG. 10A shows human sperm ($2-20\times10^7$ cells) were suspended in PBS (first far left column) and added with the irrelevant MAPS peptide (second column), alanine-MAPS (third column) and GWRQ-MAPS (fourth column). The number of motile sperm were determined after incubation at room temperature for 30 min. GWRQ-MAPS enhanced sperm motility in cases 1-3 but did not affect sperm in case 4.

When human sperm suspended in PBS were visually inspected under a phase contrast microscope, it was noted that when GWRQ-MAPS was added, sperm moved more vigorously. To determine the effect of GWRQ-MAPS on human sperm motility, human sperm from four healthy men was tested and sperm motility counted as described above in PBS without peptide, with an irrelevant MAPS, with alanine-MAPS, and with GWRQ-MAPS. This analysis showed that GWRQ-MAPS enhanced sperm motility in three cases, but it did not affect sperm motility from the fourth (FIG. 10A). This observation indicates that GWRQ-MAPS can enhance motility of human sperm, but this does not apply to the sperm from all individuals.

Figure 10B:
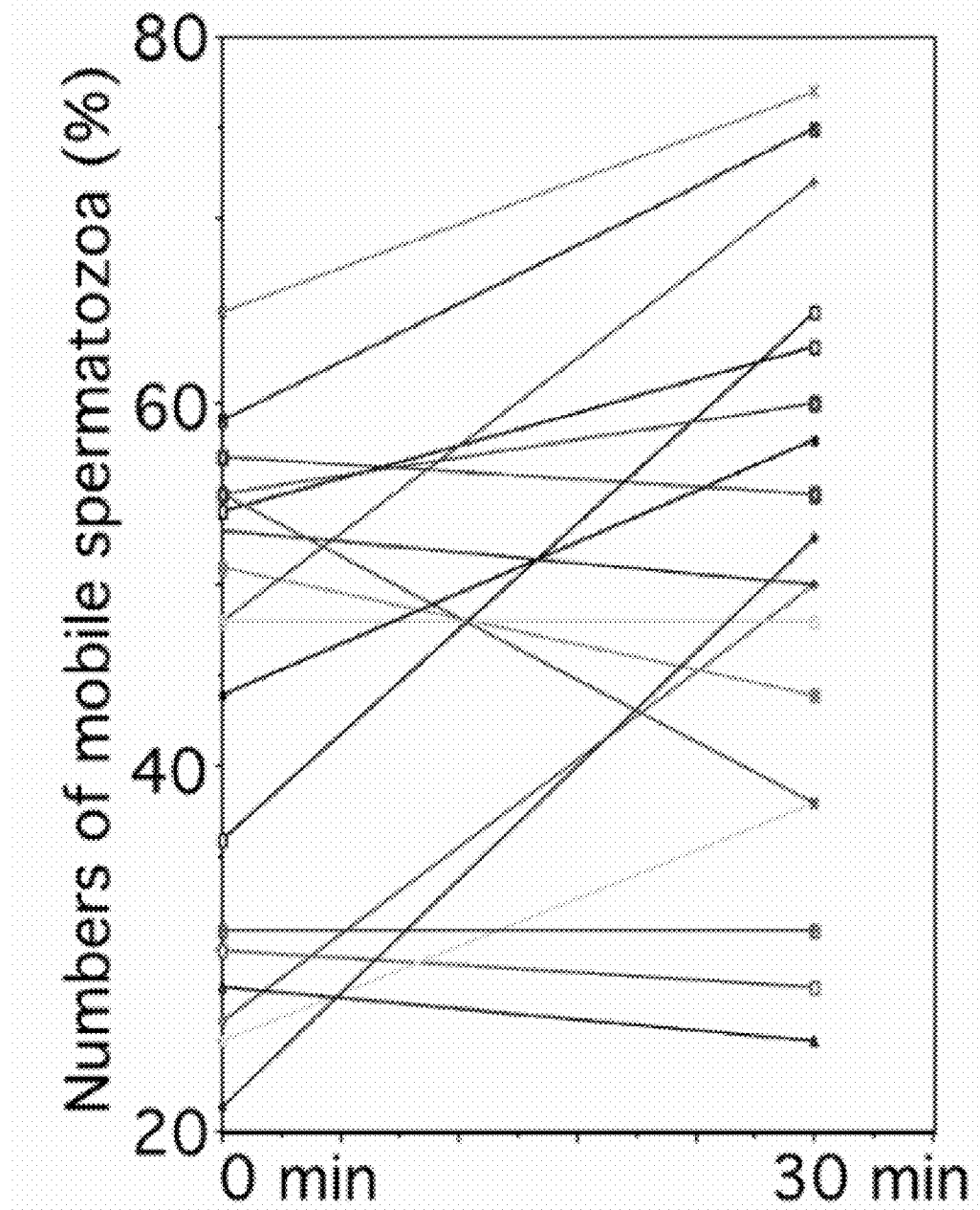
FIG. 10B left shows numbers of mobile sperm from each donor were counted at time 0 after washing with PBS and 30 minutes after incubation with GWRQ-MAPS. Cases of which the sperm showed high (more than 70%) or low (less than 20%) mobility at time 0 were excluded.
Figure 10C:
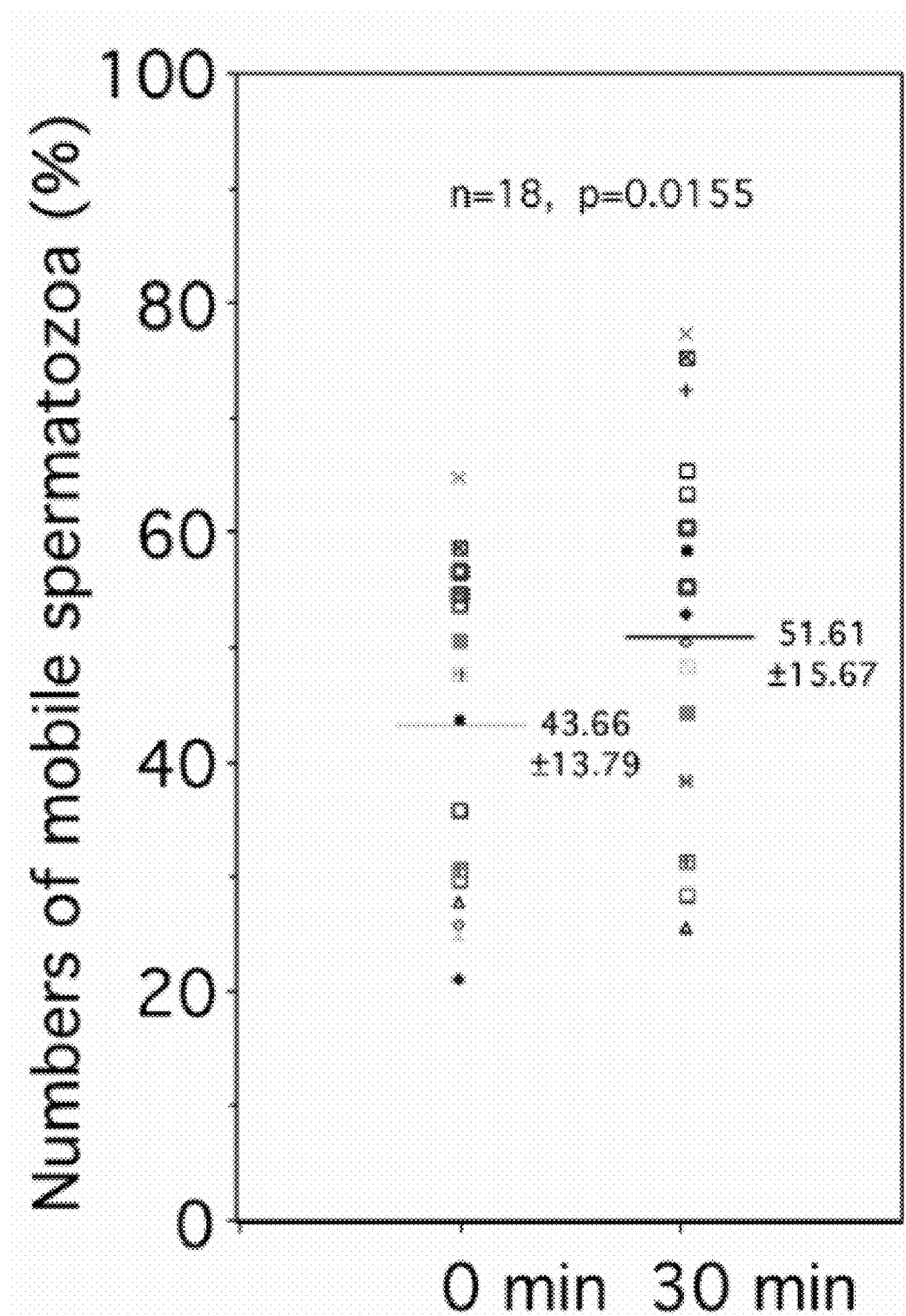
FIG. 10C right shows statistical analysis of data shown in left.

To confirm the above-described results, sperm from a larger number of subjects was tested (FIG. 10B,C). In this analysis, individuals were excluded at either extreme; i.e., more than 70% or less than 20% of motile sperm in PBS. Statistical analysis showed that significant (p<0.05, Wilcoxon signed-rank test) numbers of individuals showed elevated sperm motility in the presence of GWRQ-MAPS.

b. The Presence of Trophinin, Bystin and Tastin Proteins in Human Sperm

GWRQ-MAPS binds to the extracellular domain of trophinin in trophoblastic cells and transmits a signal to the cytoplasm (Sugihara, K., et al. 2007). The cytoplasmic domain of trophinin interacts with bystin and tastin (Suzuki, N., et al. 1998) and tastin binds to microtubules (Nadano, D., et al. 2002). Immunohistochemistry of intact human sperm detected a strong trophinin signal in the neck portion of sperm, but no signal was seen in the tail. Strong trophinin immunostaining was previously shown in the tail using a rabbit antibody against the trophinin cytoplasmic domain (Saburi, S., et al. 2001), but here a monoclonal antibody targeting the extracellular domain was used. Sperm tails were stained strongly by antibody specific to large acidic polysialic acid carbohydrates, which can impair the penetration of an antibody to the extracellular domain of the protein. Indeed, after mild acid treatment to hydrolyze polysialic acid (Inoue, S., et al. 2001), the sperm tail showed positive trophinin staining. These results showed the presence of trophinin protein in the neck, mid-piece and tail portions of human sperm.

Intact human sperm stained for trophinin showed signals at the lower head portion. Tails were not stained under these conditions. Human sperm smeared on a glass slide were fixed with 4% paraformaldehyde in PBS and treated with 0.1 N HCl at 80° C. for 1 hour. Acid treated sperm were immunostained for trophinin, showing signals in the tail. Fixed sperm were permeabilized by methanol and stained for bystin and tastin. Fixed and acid-treated sperm were incubated with control phage or with GWRQ peptide-displaying phage, and bound phage was detected by anti-phage fd antibody.

Immunohistochemistry of human sperm for bystin and tastin showed the presence of bystin and tastin in the mid-piece and tail of human sperm. Immunostainings for trophinin, bystin, and tastin in sperm tail showed the stripe. These staining patterns indicates that trophinin, bystin, and tastin proteins co-localize in the sperm tail.

Since GWRQ-MAPS affects sperm motility, it was asked whether it bound to human sperm. Immunohistochemistry with acid-treated sperm showed that GWRQ-displaying phage bound to the tail. Control phage without the displayed peptide did not bind to the tail of acid-treated sperm. A signal for GWRQ-displaying phage was not detected on sperm tail without acid treatment.

c. Effect of GWRQ Peptide on ATP and Intracellular $Ca^{2+}$.

Figure 11A:
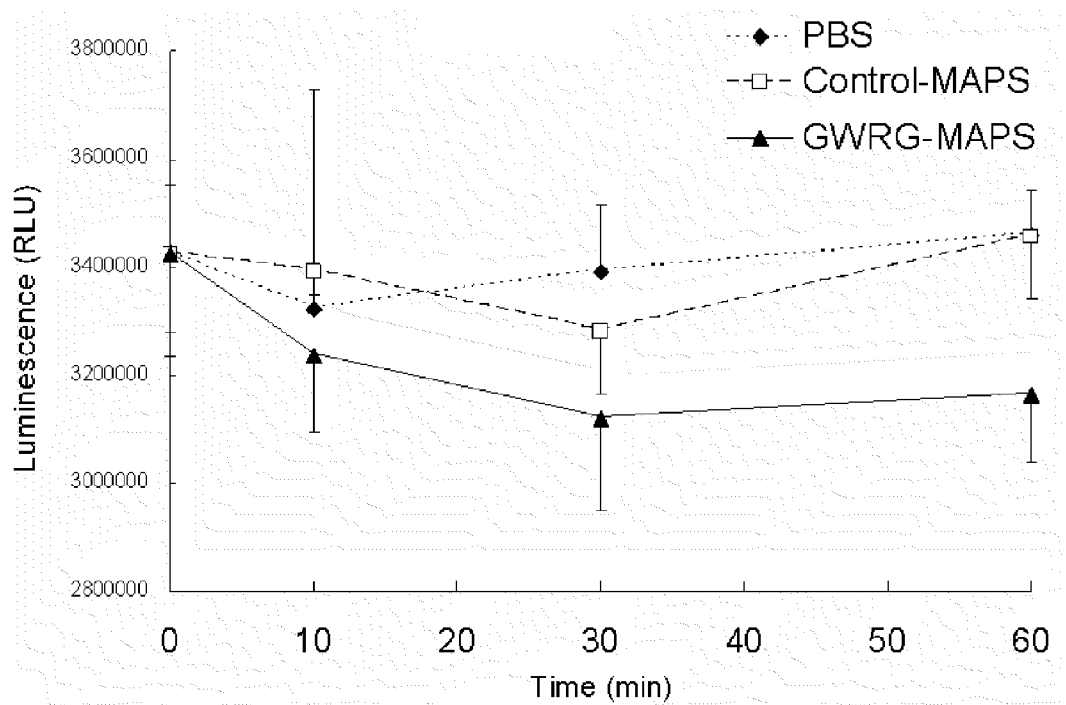
FIG. 11A shows ATP levels were analyzed at 0, 10, 30, and 60 min after adding PBS containing control-MAPS and GWRQ-MAPS (15 µg/ml each). Each value represents the average of 8 readings, and each bar represents the standard deviation. Sperm with GWRQ-MAPS showed statistically significant ($p<0.01$, t-test) reduction in ATP levels at 30 min and 60 min compared to controls.

Since dynein ATPase plays a critical role in sperm tail motility, ATP levels were determined in human sperm in medium with or without GWRQ-MAPS (FIG. 11A). ATP levels were reduced over time in human sperm cells incubated in medium alone or in medium containing control peptide, reflecting ATP consumption by ATPase. In sperm cells incubated with GWRQ-MAPS-containing medium, ATP levels were reduced more rapidly than in controls (p<0.01, t-test). These results are consistent with GWRQ-MAPS enhancing ATPase activity by releasing dynein from a trophinin-bystin-tastin complex in the sperm tail.

Figure 11B:
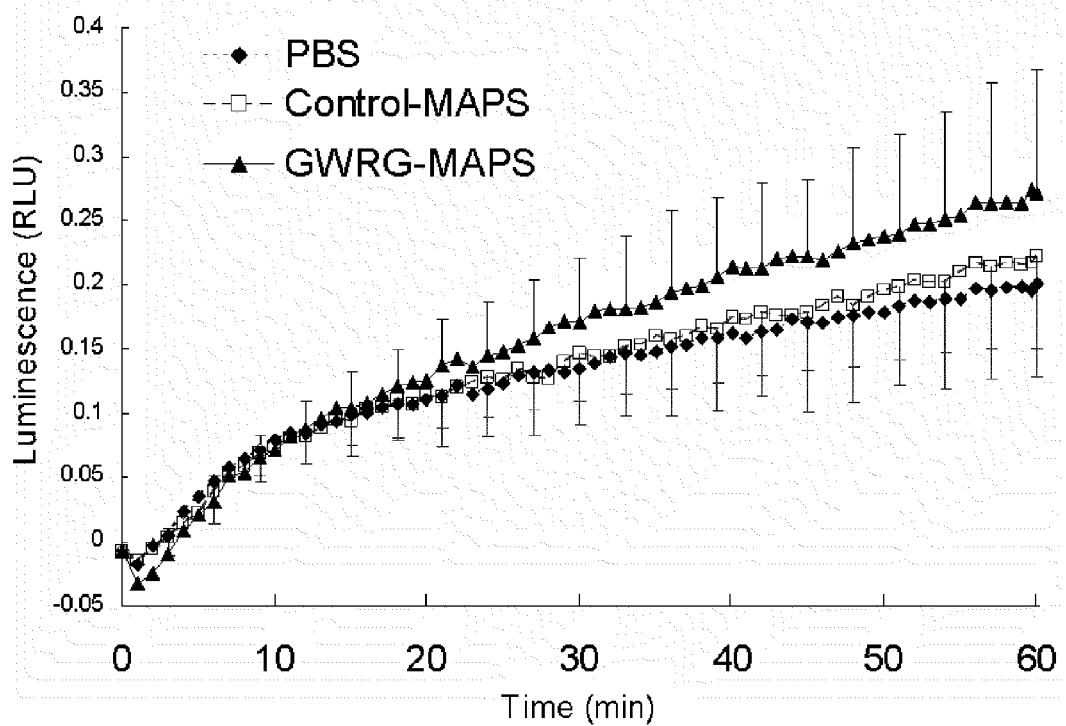
FIG. 11B shows intracellular calcium in human sperm was measured between time 0 and 60 min in PBS with either control-MAPS or GWRQ-MAPS (15 µg/ml each). Calcium concentration was elevated by GWRQ-MAPS.

Since sperm motility is closely linked to activity of $Ca^{2+}$ channels, such as cyclic AMP-gated ion channels (Ren, D., et al. 2001; Schuh, K., et al. 2004; Okunade, G. W., et al. 2004; Qi, H., et al. 2007), intracellular $Ca^{2+}$ was compared in human sperm incubated in medium with or without GWRQ-MAPS (FIG. 11B). Intracellular $Ca^+$ was significantly (p<0.01, t-test) increased in sperm cells incubated with medium containing GWRQ-MAPS compared to cells incubated in medium containing control peptide or no peptide. These results indicate that GWRQ-MAPS activates cytoplasmic proteins leading to activation of $Ca^{2+}$ channel.

d. Effect of GWRQ-MAPS on Directed Sperm Motility.

Most mammalian sperm display two types of physiological motility: activated motility and hyperactivated motility (Katz, D. F., et al. 1980; Demott, R. P., et al. 1992). Activated motility drives the sperm in a relatively straight line. By contrast, hyperactivated motility enforces asymmetrical and higher amplitude tail beat, which results in circular or figure-eight trajectories (Yanagimachi, R. 1970; Suarez, S. S., et al. 2003; Ishijima, S., et al. 2002).

It was frequently observed that GWRQ-treated sperm moved in circular trajectories. Thus it was asked whether GWRQ-MAS enhances activated motility. In a "swim-up" assay, when sperm cells were placed in the lower chamber and the number of sperm migrating to the upper chamber through filter pores was counted, no difference was detected between sperm incubated with or without GWRQ-MAPS, indicating that GWRQ-MAPS treatment cannot enhance a long distance, forward movement.

Figure 12:
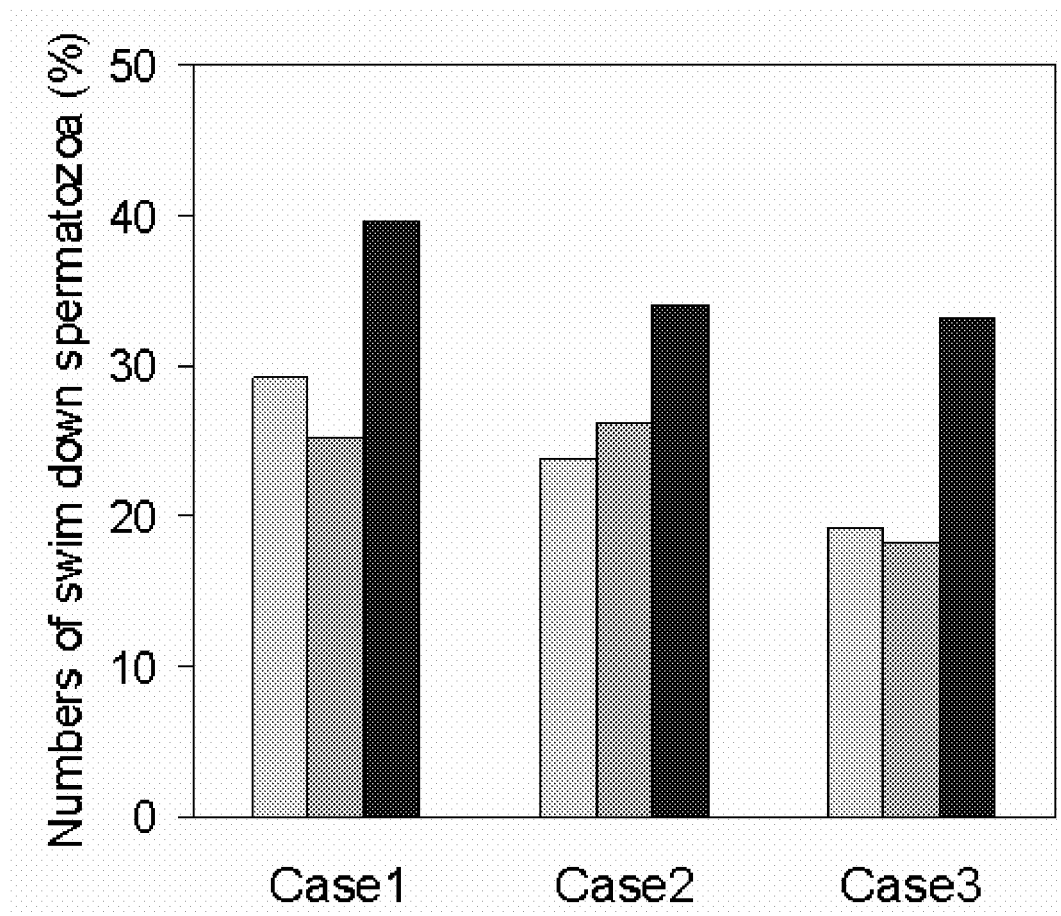
FIG. 12 shows effect of GWRQ peptide on swim-down motility. Human sperm ($2.2-2.8\times10^6$ cells/100 µl) from healthy men were suspended in sperm washing medium in a transwell culture chamber with an 8 µm pore and incubated with PBS (first far left column), with control-peptide (second column) or with GWRQ-MAPS (third column). The peptide concentration was 5 mg/ml in case 1, and 15 mg/ml in cases 2 and 3. The numbers of motile sperm in the lower chamber were determined after incubation at 37° C. for 2 hr. Note that GWRQ-MAPS enhanced swim-down sperm motility in all cases.

On the other hand, in a "swim-down" assay in which sperm cells were placed in the upper chamber and the numbers of sperm moving to the lower chamber were counted, a significant increase in the number of sperm migrating through the pores was seen when the media contained GWRQ-MAPS. Human sperm was tested from 3 healthy men and in all cases enhanced sperm migration was observed (FIG. 12). This result indicates that GWRQ-MAPS treatment also enhances short distance forward movement.

iv. Discussion

Successful fertilization in a large animal requires sperm to travel long distances prior to reaching the female egg. Because the sperm is a fully differentiated cell that does not grow, the sperm cell must conserve a limited energy supply to survive. The present study indicates a mechanism for conserving energy in human sperm by trophinin and trophinin-associated proteins. In some aspects, the peptide can be used for in vitro fertilization, as this procedure uses small volume of medium.

Although trophinin was originally identified as a plasma membrane protein mediating apical cell adhesion between trophectoderm and endometrial epithelia in human embryo implantation, trophinin is strongly expressed in brain, ovary, and testis (Nadano, D., et al. 2002; Saburi, S., et al. 2001), indicating specific roles in these tissues. The trophinin knock-out mouse does not show an obvious defect in any of these organs, making it difficult to analyze trophinin function in systems other than trophoblastic cells and endometrial epithelial cells involved in embryo implantation (Nadano, D., et al. 2002). The present study was prompted by the observation of sperm immobility in trophinin null mice. The availability of a trophinin-binding peptide, GWRQ-MAPS (Sugihara, K., et al. 2007), enabled the evaluation of the role of trophinin in human sperm.

Immunohistochemistry of mouse testes with a polyclonal rabbit antibody raised against the trophinin cytoplasmic domain detected strong signals in sperm tails (Saburi, S., et al. 2001). The monoclonal anti-trophinin antibody used here was raised against the extracellular domain of trophinin (Suzuki, N., et al. 1999). That antibody detected a strong trophinin signal at the neck portion of the sperm head but did not show the trophinin in the mid-piece and tail. However, after mild acid hydrolysis to remove polysialic acid, sperm tails were immunostained by the antibody. Similarly, GWRQ-displaying phage bound to the tail of human sperm only after mild acid hydrolysis. These results indicate that polysialic acid prevents access to sperm by large molecules or particles, such as antibodies or phage. Polysialic acid may function to prevent sperm tails from self-aggregating through trophinin-trophinin binding.

Trophinin is an integral membrane protein with its N-terminal region in the cytoplasm and unique decapeptide repeats on the cell surface (Fukuda, M. N., et al. 1995). An evolutionarily conserved cytoplasmic protein, bystin (Suzuki, N., et al. 1998; Miyoshi, M., et al. 2007; Chen, W., et al. 2003; Stewart, M. J. 2005; Adachi, K., et al. 2007; Fukuda, M. N., 2007), binds to the trophinin cytoplasmic domain (Suzuki, N., et al. 1998). Bystin also binds to the proline-rich microtubule-associated protein tastin (Suzuki, N., et al. 1998; Nadano, D., et al. 2002). Yeast two hybrid library screening showed that tastin binds to Tctex-1, the light chain of the microtubule-associated ATPase dynein (Nadano, D., et al. 2002). When dynein ATPase is activated by phosphorylation, sperm tails beat as ATP hydrolysis is converted to force, causing microtubules to slide against one another. In sperm, ATP is generated by mitochondria located at the mid piece between the head and tail and must travel a distance to supply energy to dyneins in the tail. In order to achieve a long travel, ATPs produced in mitochondria should be supplied to the rest of the flagellum without premature hydrolysis. As the size of sperm is not significantly different in small or large animals, well-regulated ATP consumption seems to be critical for a large animal for successful fertilization.

Several studies indicate an important role for calcium in sperm motility. For example, mice deficient in the plasma membrane $Ca^{2+}$/calmodulin-dependent $Ca^{2+}$ ATPase (PMCA) show impaired sperm motility and infertility (Schuh, K., et al. 2004), and ablation of the cation channel of sperm (CatSper) is associated with infertility due to impaired sperm motility (Okunade, G. W., et al. 2004). Mice lacking the mitochondrial voltage-dependent anion channel type 3 (VDAC3) are also infertile due to immotile sperm (Sugihara, K., et al. 2007). These results show that tight regulation of ion entry by ion channels is critical to sperm function.

It is estimated that 20% of couples are infertile, and about half of infertility cases is attributable to the male partner (de Kretser, D. M. 1997). The clinical practice of in vitro fertilization employs intra cytoplasmic sperm injection (ICSI), which overcomes infertility due to sperm immobility (Van Steirteghem, A. C., et al. 1993; Hansen, M., et al. 2002). If GWRQ-MAPS can enhance motility of sperm from infertile male patients in vitro, GWRQ-MAPS can improve in vitro fertilization as an alternative to ICSI.

3. Example 3

The Trophinin-Binding Peptide GWRQ Promotes Neuronal Growth

Rat E18 spinal cord cells were obtained from Genlantis, San Diego. The cells were cultured in plastic tissue culture dish using medium provided by Genlantis with or without GWRQ-MAPS peptide (5 mg/ml).

Ten days later, the culture without GWRQ-MAPS showed no survived cells. By contrast, the culture with GWRQ-MAPS showed neuronal cells. In the same dish, there were colonies composed of flat epithelial-like cells. These flat cells were not found in control culture.

Medium containing GWRQ-MAPS was then replaced with medium without. One day after this medium change (10+1), flat cells shrank.

Five-six days after culturing without GWRQ-MAPS, cells showed neuron-like morphology.

G. REFERENCES

Adachi, K., Soeta-Saneyoshi, C., Sagara, H. and Iwakura, Y. (2007) Crucial role of Bysl in mammalian preimplantation development as an integral factor for 40S ribosome biogenesis. Mol Cell Biol 27, 2202-14.

Aoki, R., Suzuki, N., Paria, B. C., Sugihara, K., Akama, T. O., Raab, G., Miyoshi, M., Nadano, D. and Fukuda, M. N. (2006) The Bysl gene product, bystin, is essential for survival of mouse embryos. FEBS Lett 580, 6062-8.

Bavister, B. D. & Yanagimachi. The effects of sperm extracts and energy sources on the motility and acrosome reaction of hamster spermatozoa in vitro. Biol. Reprod. 16, 228-37 (1977).

Blume-Jensen, P. & Hunter, T. Oncogenic kinase signalling. Nature 411, 355-65 (2001).

Brenner, P. F., Roy, S. & Mishell, D. R., Jr. Ectopic pregnancy. A study of 300 consecutive surgically treated cases. Jama 243, 673-6 (1980).

Carpenter, G. The EGF receptor: a nexus for trafficking and signaling. Bioessays 22, 697-707 (2000).

Carson, D. D. et al. Embryo implantation. Dev. Biol. 223, 217-237 (2000).

Cavallaro, U. & Christofori, G. Multitasking in tumor progression: signaling functions of cell adhesion molecules. Ann. N.Y. Acad. Sci. 1014, 58-66 (2004)

Chen, W., Bucaria, J., Band, D. A., Sutton, A. and Stemglanz, R. (2003) Enp1, a yeast protein associated with U3 and U14 snoRNAs, is required for pre-rRNA processing and 40S subunit synthesis. Nucleic Acids Res 31, 690-9.

Chobotova, K. et al. Heparin-binding epidermal growth factor and its receptor ErbB4 mediate implantation of the human blastocyst. Mech. Dev. 119, 137-44 (2002).

Das, S. K. et al. Heparin-binding EGF-like growth factor gene is induced in the mouse uterus temporally by the blastocyst solely at the site of its apposition: a possible ligand for interaction with blastocyst EGF-receptor in implantation. Development 120, 1071-1083 (1994).

de Kretser, D. M. (1997) Male infertility. Lancet 349, 787-90.

Demott, R. P. and Suarez, S. S. (1992) Hyperactivated sperm progress in the mouse oviduct. Biol Reprod 46, 779-85.

Enders, A. C. Cytology of human early implantation. Res Reprod 8, 1-2 (1976).

Enders, A. C., Lantz, K. C., Peterson, P. E. & Hendrick, A. G. From blastocyst to placenta: the morphology of implantation in the baboon. Human Reprod. update 12, 309-325 (1997).

Fukuda, M. N. & Nozawa, S. Trophinin, tastin, and bystin: a complex mediating unique attachment between trophoblastic and endometrial epithelial cells at their respective apical cell membranes. Semin. Reprod. Endocrinol. 17, 229-34 (1999).

Fukuda, M. N. et al. A peptide mimic of E-selectin ligand inhibits sialyl Lewis X-dependent lung colonization of tumor cells. Cancer Res. 60, 450-6 (2000).

Fukuda, M. N. et al. Trophinin and tastin, a novel cell adhesion complex with potential involvement in embryo implantation. Genes & Develop. 9, 1199-1210 (1995).

Fukuda, M. N., Nadano, D., Suzuki, N. & Nakayama, J. in Embryo Implantation: Molecular, Cellular and Clinical Aspects. (ed. Carson, D. D.) 132-140 (Serono Symposia USA, Norwell, Mass., 1999).

Fukuda, M. N. and Sugihara, K. (2007) Signal transduction in human embryo implantation. Cell Cycle 6, 1153-6.

Fukada, M. N., Miyoshi, M. and Nadano, D. (2007) The role of bystin in embryo implantation and in ribosomal biogenesis. Cell Mol Life Sci. 2007 Oct. 6 [Epub]

Giancotti, F. G. & Ruoslahti, E. Integrin signaling. Science 285, 1028-32 (1999).

Gratzner, H. G. Monoclonal antibody to 5-bromo- and 5-iododeoxyuridine: A new reagent for detection of DNA replication. Science 218, 474-475 (1982).

Hansen, M., Kurinczuk, J. J., Bower, C. and Webb, S. (2002) The risk of major birth defects after intracytoplasmic sperm injection and in vitro fertilization. N Engl J Med 346, 725-30.

Hertig, A. T. & Rock, J. Searching for early fertilized human ova. Gynecol. Invest. 4, 121-39 (1973).

Hertig, A. T., Rock, J. & Adams, E. C. A description of 34 human ova within the first 17 days of development. Am. J. Anat. 98, 435-93 (1956).

Inoue, S, and Inoue, Y. (2001) Developmental profile of neural cell adhesion molecule glycoforms with a varying degree of polymerization of polysialic acid chains. J Biol Chem 276, 31863-70.

Ishijima, S., Baba, S. A., Mohri, H. and Suarez, S. S. (2002) Quantitative analysis of flagellar movement in hyperactivated and acrosome-reacted golden hamster spermatozoa. Mol Reprod Dev 61, 376-84.

Katz, D. F. and Vanagimachi, R. (1980) Movement characteristics of hamster spermatozoa within the oviduct. Biol Reprod 22, 759-64.

Knoth, M. & Larsen, J. F. Ultrastructure of a human implantation site. Acta Obst. Gynecol. Scand. 51, 385-393 (1972).

Koivunen, E., Wang, B. & Ruoslahti, E. Isolation of a highly specific ligand for the alpha 5 beta 1 integrin from a phage display library. J. Cell Biol. 124, 373-80 (1994).

Komuro, A., Nagai, M., Navin, N. E. & Sudol, M. WW domain-containing protein YAP associates with ErbB-4 and acts as a co-transcriptional activator for the carboxyl-terminal fragment of ErbB-4 that translocates to the nucleus. J. Biol. Chem. 278, 33334-41 (2003).

Lindenberg, S., Hyttel, P., Lenz, S. & Holmes, P. V. Ultrastructure of the early human implantation in vitro. Human Reprod. 1, 533-538 (1986).

McKiernan, S. H. & Bavister, B. D. Culture of one-cell hamster embryos with water soluble vitamins: pantothenate stimulates blastocyst production. Hum. Reprod. 15, 157-64 (2000).

Millan, J.-L. & Stigbrand, T. Antigenic determinants of human placental and testicular placental-like alkaline phosphatase as mapped by monoclonal antibodies. Eur. J. Biochem. 136, 1-7 (1983).

Miyoshi, M., Okajima, T., Matsuda, T., Fukuda, M. N. and Nadano, D. (2007) Bystin in human cancer cells: intracellular localization and function in ribosome biogenesis. Biochem J 404, 373-81.

Nadano, D. et al. Human tastin, a proline-rich cytoplasmic protein, associates with the microtubular cytoskeleton. Biochem. J. 364, 669-77 (2002).

Nadano, D., Sugihara, K., Paria, B. C., Saburi, S., Copeland, N. G., Gilbert, D. J., Jenkins, N. A., Nakayama, J. and Fukuda, M. N. (2002) Significant differences between mouse and human trophinins are revealed by their expression patterns and targeted disruption of mouse trophinin gene. Biol Reprod 66, 313-21.

Nakayama, J. et al. Implantation-Dependent Expression of Trophinin by Maternal Fallopian Tube Epithelia during Tubal Pregnancies: Possible Role of Human Chorionic Gonadotrophin on Ectopic Pregnancy. Am. J. Pathol. 163, 2211-9 (2003).

Narisawa, S., Hecht, N. B., Goldberg, E., Boatright, K. M., Reed, J. C. and Millan, J. L. (2002) Testis-specific cytochrome c-null mice produce functional sperm but undergo early testicular atrophy. Mol Cell Biol 22, 5554-62.

Okunade, G. W., Miller, M. L., Pyne, G. J., Sutliff, R. L., O'Connor, K. T., Neumann, J. C., Andringa, A., Miller, D. A., Prasad, V., Doetschman, T., Paul, R. J. and Shull, G. E. (2004) Targeted ablation of plasma membrane Ca2+-ATPase (PMCA) 1 and 4 indicates a major housekeeping function for PMCA1 and a critical role in hyperactivated sperm motility and male fertility for PMCA4. J Biol Chem 279, 33742-50.

Orsini, M. W. & McLaren, A. Loss of the zona pellucida in mice, and the effect of tubal ligation and ovariectomy. J. Reprod. Fertil. 13, 485-499 (1967).

Padykula, H. A. in Histology (ed. Weiss, L.) 966-999 (Elsevier Biomedical, 1983).

Paria, B. C., Elenius, K., Klagsbrun, M. & Dey, S. K. Heparin-binding EGF like growth factor interacts with mouse blastocysts independently of ErbB1: a possible role for heparan sulfate proteoglycans and ErbB4 in blastocyst implantation. Development 126, 1997-2005 (1999).

Paria, B. C., Reese, J., Das, S. K. & Dey, S. K. Deciphering the cross-talk of implantation: advances and challenges. Science 296, 2 185-8 (2002).

Qi, H., Moran, M. M., Navarro, B., Chong, J. A., Krapivinsky, G., Krapivinsky, L., Kirichok, Y., Ramsey, I. S., Quill, T. A. and Clapham, D. E. (2007) All four CatSper ion channel proteins are required for male fertility and sperm cell hyperactivated motility. Proc Natl Acad Sci USA 104, 1219-23.

Ren, D., Navarro, B., Perez, G., Jackson, A. C., Hsu, S., Shi, Q., Tilly, J. L. and Clapham, D. E. (2001) A sperm ion channel required for sperm motility and male fertility. Nature 413, 603-9.

Saburi, S., Nadano, D., Akama, T. O., Hirama, K., Yamanouchi, K., Naito, K., Tojo, H., Tachi, C. and Fukuda, M. N. (2001) The trophinin gene encodes a novel group of MAGE proteins, magphinins, and regulates cell proliferation during gametogenesis in the mouse. J. Biol. Chem. 276, 49378-49389.

Schuh, K., Cartwright, E. J., Jankevics, E., Bundschu, K., Liebermann, J., Williams, J. C., Armesilla, A. L., Emerson, M., Oceandy, D., Knobeloch, K. P. and Neyses, L. (2004) Plasma membrane Ca2+ ATPase 4 is required for sperm motility and male fertility. J Biol Chem 279, 28220-6.

Stewart, M. J. and Nordquist, E. K. (2005) *Drosophila* Bys is nuclear and shows dynamic tissue-specific expression during development. Dev Genes Evol 215, 97-102.

Suarez, S. S. and Ho, H. C. (2003) Hyperactivated motility in sperm. Reprod Domest Anim 38, 119-24.

Sugihara, K., Sugiyama, D., Byrne, J., Wolf, D. P., Lowitz, K. P., Kobayashi, Y., Kabir-Salmani, M., Nadano, D., Aoki, D., Nozawa, S., Nakayama, J., Mustelin, T., Ruoslahti, E., Yamaguchi, N. and Fukuda, M. N. (2007) Trophoblast cell activation by trophinin ligation is implicated in human embryo implantation. Proc Natl Acad Sci USA 104, 3799-804.

Summers, K. E. and Gibbons, I. R. (1971) Adenosine triphosphate-induced sliding of tubules in trypsin-treated flagella of sea-urchin sperm. Proc Natl Acad Sci USA 68, 3092-6.

Suzuki, N. et al. A novel cytoplasmic protein, bystin, interacts with trophinin, tastin and cytokeratin, and may be involved in trophinin mediated cell adhesion between trophoblast and endometrial epithelial cells. Proc. Natl. Acad. Sci. USA 95, 5027-5032 (1998).

Suzuki, N. et al. Expression of trophinin, tastin, and bystin by trophoblast and endometrial cells in human placenta. Biol. Reprod. 60, 621-627 (1999).

Suzuki, N., Nadano, D., Paria, B. C., Kupriyanov, S., Sugihara, K. and Fukuda, M. N. (2000) Trophinin expression in the mouse uterus coincides with implantation and is hormonally regulated but not induced by implanting blastocysts. Endocrinology 141, 4247-54.

Suzuki, N., Zara, J., Sato, T., Ong, E., Bakhiet, N., Oshima, R. G., Watson, K. L. and Fukuda, M. N. (1998) A novel cytoplasmic protein, bystin, interacts with trophinin, tastin and cytokeratin, and may be involved in trophinin mediated cell adhesion between trophoblast and endometrial epithelial cells. Proceedings of the National Academy of Sciences, USA 95, 5027-5032.

Swaffield, J. C. & Johnson, S. A. in Current Protocol in Molecular Biology 20.2.1-20.2. 10 (John Wiley & Sons, Inc., 1996).

Tada, J., Omine, M., Suda, T. & Yamaguchi, N. A common signaling pathway via Syk and Lyn tyrosine kinases generated from capping of the sialomucins CD34 and CD43 in immature hematopoietic cells. Blood 93, 3723-35 (1999).

Tash, J. S. and Means, A. R. (1987) Ca2+ regulation of sperm axonemal motility. Methods Enzymol 139, 808-23.

Threadgill, D. W. et al. Targeted disruption of mouse EGF receptor: effect of genetic background on mutant phenotype. Science 269, 230-4 (1995).

Turner, R. M. (2003) Tales from the tail: what do we really know about sperm motility? J Androl 24, 790-803.

Van Steirteghem, A. C., Nagy, Z., Joris, H., Liu, J., Staessen, C., Smitz, J., Wisanto, A. and Devroey, P. (1993) High fertilization and implantation rates after intracytoplasmic sperm injection. Hum Reprod 8, 1061-6.

Wilde, A. et al. EGF receptor signaling stimulates SRC kinase phosphorylation of clathrin, influencing clathrin redistribution and EGF uptake. Cell 96, 677-87 (1999).

Wolf, D. P. et al. Use of assisted reproductive technologies in the propagation of rhesus macaque offspring. Biol. Reprod. 71, 486-93 (2004).

Yamaguchi, N. & Fukuda, M. N. Golgi retention mechanism of β-1,4-galactosyltransferase. Membrane spanning domain dependent homodimerization and association with α- and β-tubulins. J. Biol. Chem. 270, 12170-12176 (1995).

Yanagimachi, R. (1970) The movement of golden hamster spermatozoa before and after capacitation. J Reprod Fertil 23, 193-6.

Zelinski-Wooten, M. B., Hutchison, J. S., Hess, D. L., Wolf, D. P. & Stouffer, R. L. Follicle stimulating hormone alone supports follicle growth and oocyte development in gonadotrophin-releasing hormone antagonist-treated monkeys. Hum. Reprod. 10, 1658-66 (1995).

H. SEQUENCES

1. SEQ ID NO:1

$X_1X_2X_3X_4$, where $X_1$=G, A, L, I, T, or S; $X_2$=W or Y; $X_3$=R, K, or H; and $X_4$=Q or N

---

What is claimed is:

1. A method of promoting sperm motility, comprising contacting the sperm in vitro with an isolated polypeptide comprising one or more trophinin-binding segments, wherein at least one of the trophinin-binding segments comprises the amino acid sequence $X_1X_2X_3X_4$ (SEQ ID NO:1), wherein $X_1$ is G, A, L, I, T, or S;
$X_2$ is W or Y;
$X_3$ is R, K, or H; and
$X_4$ is Q or N,
wherein the polypeptide is 50 amino acids or less in length.

2. The method of claim 1, wherein the sperm is used for in vitro fertilization.

3. The method of claim 2, wherein fertilization is increased by at least about 10%, 20%, 30%, 40%, 50%, or higher.

4. A method of promoting sperm motility, comprising contacting the sperm in vitro with an isolated polypeptide comprising one or more trophinin-binding segments, wherein at least one of the trophinin-binding segments comprises the amino acid sequence $X_1X_2X_3X_4$ (SEQ ID NO:1), wherein $X_1$ is G;
$X_2$ is W;
$X_3$ is R; and
$X_4$ is Q.

5. The method of claim 4, wherein the at least one of the trophinin-binding segments comprises the amino acid sequence GWRQLTARVP (SEQ ID NO:4), SSLMLGGWRQ (SEQ ID NO:19), or SLSVGWRQSG (SEQ ID NO:20).

6. A method of promoting sperm motility, comprising administering to a subject an isolated polypeptide comprising one or more trophinin-binding segments, wherein at least one of the trophinin-binding segments comprises the amino acid sequence $X_1X_2X_3X_4$ (SEQ ID NO:1), wherein $X_1$ is G, A, L, I, T, or S;
$X_2$ is W or Y;
$X_3$ is R, K, or H; and
$X_4$ is Q or N,
wherein the polypeptide is 50 amino acids or less in length.

7. The method of claim 1, wherein the at least one trophinin-binding segment comprises the amino acid sequence $X_1X_2X_3X_4X_5$ (SEQ ID NO:3), wherein $X_5$ is S, A, V, or L.

8. The method of claim 1, wherein at least one trophinin-binding segment comprises the amino acid sequence GWRQ (SEQ ID NO:2).

9. The method of claim 1, wherein the polypeptide selectively binds trophinin.

10. The method of claim 1, wherein each trophinin-binding segment independently consists of from 4 to 50 amino acids.

11. The method of claim 1, wherein at least one trophinin-binding segment comprises the amino acid sequence GWRQLTARVP (SEQ ID NO:4).

12. The method of claim 1, wherein at least one trophinin-binding segment consists essentially of the amino acid sequence GWRQLTARVP (SEQ ID NO:4).

13. The method of claim 1, wherein the peptide has a length of less than 20 residues.

14. The method of claim 1, wherein the polypeptide binds to the extracellular domain of trophinin.

15. The method of claim 1, wherein polypeptide inhibits the bystin-mediated arrest of epidermal growth factor (EGF) receptor and promotes EGF receptor autophosphorylation.

16. The method of claim 1, wherein the polypeptide comprises two or more trophinin-binding segments.

17. The method of claim 1, wherein the polypeptide comprises two or more amino acid branches.

18. The method of claim 17, wherein the polypeptide further comprises a peptidyl core of 2, 3, 4, 5, 6, 7, 8, 9, 10 or more branched lysine residues, wherein two or more of the trophinin-binding segments are linked to two or more branched lysine residues.

* * * * *